US006262018B1

(12) United States Patent
Kim et al.

(10) Patent No.: US 6,262,018 B1
(45) Date of Patent: Jul. 17, 2001

(54) HYPERSENSITIVE RESPONSE ELICITOR FROM *ERWINIA AMYLOVORA* AND ITS USE

(75) Inventors: Jihyun Francis Kim; Steven V. Beer, both of Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/120,927

(22) Filed: Jul. 22, 1998

Related U.S. Application Data

(60) Provisional application No. 60/055,108, filed on Aug. 6, 1997.

(51) Int. Cl.[7] .............................. A01H 9/00; A01H 11/00; A01H 5/00; A61K 38/100; A61K 38/00

(52) U.S. Cl. .............................. 514/2; 435/71.1; 435/410; 435/418; 530/825; 530/300; 800/298; 800/295; 514/12

(58) Field of Search .............................. 530/825, 300; 536/23.1, 23.7, 71.1; 435/418, 410; 800/298, 295; 514/12

(56) References Cited

U.S. PATENT DOCUMENTS

| | | | |
|---|---|---|---|
| 4,569,841 | 2/1986 | Liu | 424/93.4 |
| 4,597,972 | 7/1986 | Taylor | 426/36 |
| 4,601,842 | 7/1986 | Caple et al. | 252/70 |
| 4,740,593 | 4/1988 | Gonzalez et al. | 422/1 |
| 4,851,223 | 7/1989 | Sampson | 424/711 |
| 4,886,825 | 12/1989 | Ruess et al. | 514/383 |
| 4,931,581 | 6/1990 | Schurter et al. | 560/18 |
| 5,057,422 | 10/1991 | Bol et al. | 424/93.47 |
| 5,061,490 | 10/1991 | Paau et al. | 424/93.47 |
| 5,135,910 | 8/1992 | Blackburn et al. | 514/2 |
| 5,173,403 | 12/1992 | Tang | 435/6 |
| 5,217,950 | 6/1993 | Blackburn et al. | 514/2 |
| 5,243,038 | 9/1993 | Ferrari et al. | 536/23.1 |
| 5,244,658 | 9/1993 | Parke | 504/117 |
| 5,260,271 | 11/1993 | Blackburn et al. | 514/2 |
| 5,348,743 | 9/1994 | Ryals et al. | 424/94.61 |
| 5,494,684 | 2/1996 | Cohen | 424/523 |
| 5,523,311 | 6/1996 | Schurter et al. | 514/361 |
| 5,550,228 | 8/1996 | Godiard et al. | 800/298 |
| 5,552,527 | 9/1996 | Godiard et al. | 530/379 |
| 5,650,387 | 7/1997 | Wei et al. | 514/2 |
| 5,708,139 | 1/1998 | Collmer et al. | 530/350 |
| 5,850,015 | 12/1998 | Bauer et al. | 800/279 |
| 6,001,959 | 12/1999 | Bauer et al. | 530/300 |

FOREIGN PATENT DOCUMENTS

| | | |
|---|---|---|
| 0 612 848 A3 | 8/1994 | (EP) . |
| WO 93/23532 | 11/1993 | (WO) . |
| WO 94/01546 | 1/1994 | (WO) . |
| WO 94/26782 | 11/1994 | (WO) . |
| WO 95/19443 | 7/1995 | (WO) . |
| WO 96/39802 | 12/1996 | (WO) . |
| WO 98/15547 | 4/1998 | (WO) . |
| WO 98/24297 | 6/1998 | (WO) . |
| WO 98/32844 | 7/1998 | (WO) . |
| WO 98/37752 | 9/1998 | (WO) . |
| WO 98/54214 | 12/1998 | (WO) . |
| WO 99/07206 | 2/1999 | (WO) . |
| WO 99/07207 | 2/1999 | (WO) . |

OTHER PUBLICATIONS

Linthorst et al. The Plant Cell. 1989. vol. 1: 285–291, 1989.*

Alfano et al., "Analysis of the Role of the *Pseudomonas syringae* pv. *syringae* HrpZ Harpin in Elicitation of the Hypersensitive Response in Tobacco Using Functionally Non–Polar hrpZ Deletion Mutations, Truncated HrpZ Fragments, and hrmA Mutations," *Molecular Microbiology*, 19(4):715–728 (1996).

Lorang et al., "Characterization of avrE from *Pseudomonas syringae* pv. Tomato: A hrp–Linked Avirulence Locus Consisting Of at Least Two Transcriptional Units," *MPMI* 8(1):49–57 (1995).

Malamy et al., Salicylic Acid and Plant Disease Resistance, *The Plant Journal*, 2(5):643–654 (1992).

McGurl et al., "Structure, Expression, and Antisense Inhibition of the Systemin Precursor Gene," *Science*, 255:1570–1573 (1992).

Schulte et al., "Expression of the *Xanthomonas campestris* pv. Vesicatoria hrp Gene Cluster, Which Determines Pathogenicity and Hypersensitivity on Pepper and Tomato, Is Plant Inducible," *Journal of Bacteriology*, 174(3):815–823 (1992).

Wu et al., "Disease Resistance Conferred by Expression of a Gene Encoding $H_2O_2$–Generating Glucose Oxidase in Transgenic Potato Plants," *The Plant Cell*, 7:1357–1368 (1995).

(List continued on next page.)

*Primary Examiner*—Lynette R. F. Smith
*Assistant Examiner*—Ousama Zaghmout
(74) *Attorney, Agent, or Firm*—Nixon Peabody LLP

(57) ABSTRACT

The present invention is directed to an isolated protein or polypeptide which elicits a hypersensitive response in plants as well as an isolated DNA molecule which encodes the hypersensitive response eliciting protein or polypeptide. This isolated protein or polypeptide and the isolated DNA molecule can used to impart disease resistance to plants, to enhance plant growth, and/or to control insects on plants. This can be achieved by applying the hypersensitive response elicitor protein or polypeptide in a non-infectious form to plants or plant seeds under conditions effective to impart disease resistance, to enhance plant growth, and/or to control insects on plants or plants grown from the plant seeds. Alternatively, transgenic plants or plant seeds transformed with a DNA molecule encoding a hypersensitive response elicitor protein or polypeptide can be provided and the transgenic plants or plants resulting from the transgenic plant seeds are grown under conditions effective to impart disease resistance, to enhance plant growth, and/or to control insects on plants or plants grown from the plant seeds.

6 Claims, 5 Drawing Sheets

OTHER PUBLICATIONS

Lloyd M. Yu, "Elicitins from Phytophthora and Basic Resistance in Tobacco," *Proc. Natl. Acad. Sci. USA*, 92:4088–4094 (1995).

Nissinen et al., "Clavibacter Michiganensis Subsp. Sepedonicus Elicits a Hypersensitive Response in Tobacco and Secretes Hypersensitive Response–Inducing Protein," *Phytopathology*, 87:678–684 (1997) (Abstract only).

Kloepper et al., "Enhanced Plant Growth by Siderophores Produced by Plant Growth–promoting Rhizobacteria," *Nature* 286:885–886 (1980).

Collmer et al., "*Erwinia chyrsanthemi* and *Pseudomonas syringae*: Plant Pathogens Trafficking in Extracellular Virulence Proteins," pp. 43–78.

Frederick et al., "The WTS Water–Soaking Genes of *Erwinia stewartii* are Related to hrp Genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. *glycines*," Seventh International Symposium on Molecular Plant Microbe Interactions, Abstract No. 244 (Jun. 1994).

Preston et al., "The HrpZ Proteins of *Pseudomonas syringae* pvs. *syringae, glycinea*, and *tomato* are Encoded by an Operon Containing *Yersinia ysc* Homologs and Elicit the Hypersensitive Response in Tomato but not Soybean," *Mol. Plant–Microbe Interact.*, 8(5):717–32 (1995).

Bauer et al., "*Erwinia chrysanthemi hrp* Genes and their Involvement in Elicitation of the Hypersensitive Response in Tobacco," Sixth International Symposium on Molecular Plant Microbe Interactions, Abstract No. 146 (Jul. 1992).

Stryer, L., "Enzymes are Highly Specific," *Biochemistry*, San Francisco: W.H. Freeman and Company, p. 116 (1975).

Keen et al., "Inhibition of the Hypersensitive Reaction of Soybean Leaves to Incompatible Pseudomonas spp. by Blasticidin S, Streptomycin or Elevated Temperature," *Physiological Plant Pathology*, 18:325–37 (1981).

Lerner, R.A., "Tapping the Immunological Repertoire to Produce Antibodies of Predetermined Specificity," *Nature*, 299:592–96 (1982).

Staskawicz et al., "Cloned Avirulence Gene of *Pseudomonas syringae* pv. *glycinea* Determines Race–specific Incompatibility on *Glycine max* (L.) Merr.," *Proc. Natl. Acad. Sci. USA*, 81:6024–28 (1984).

Bauer et al., "*Erwinia chrysanthemi* Harpin$_{Ech}$: An Elicitor of the Hypersensitive Response that Contributes to Soft–Rot Pathogenesis," *MPMI*, 8(4):484–91 (1995).

Huang et al., "Characterization of the hrp Cluster from *Pseudomonas syringae* pv. *syringae* 61 and TnphoA Tagging of Genes Encoding Exported or Membrane–Spanning Hrp Proteins," *Molec. Plant–Microbe Interact.*, 4(5):469–76 (1991).

Huang et al., "The *Pseudomonas syringae* pv. *syringae* 61 hrpH Product, an Envelope Protein Required for Elicitation of the Hypersensitive Response in Plants," *J. Bacteriol.*, 174(21):6878–85 (1992).

Bonas, U., "hrp Genes of Phytopathogenic Bacteria," *Current Topics in Microbio.*, 192:79–98 (1994).

Arlat et al., "PopA1, A Protein Which Induces a Hypersensitivity–Like Response on Specific Protein Petunia Genotypes, is Secreted via the Hrp Pathway of *Pseudomonas solanacearum*," *The EMBO J.*, 13(3):543–53 (1994).

Kessmann et al., "Induction of Systemic Acquired Disease Resistance in Plants By Chemicals," *Ann. Rev. Phytopathol.*, 32:439–59 (1994).

Kelman, A., "The Relationship of Pathogenicity in *Pseudomonas solanacearum* To Colony Appearance on a Tetrazolium Medium," *Phytopathology*, 44:693–95 (1954).

Winstead et al., "Inoculation Techniques For Evaluating Resistance to *Pseudomonas solanacearum,*" *Phytopathology*, 42:628–34 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Phytopathology*, 116:121–34 (1986).

Anderson et al., "Responses of Bean to Root Colonization with *Pseudomonas putida* in a Hydroponic System," *Phytopathology*, 75(9):992–95 (1985).

Gardner et al., "Growth Promotion and Inhibition by Antibiotic–Producing Fluorescent Pseudomonads on Citrus Roots," *Plant and Soil*, 77:103–13 (1984).

Kloepper, J.W., "Effect of Seed Piece Inoculation with Plant Growth–Promoting Rhizobacteria on Populations of *Erwinia carotovora* on Potato Roots and In Daughter Tubers," *Phytopathology*, 73(2):217–19 (1983).

Atkinson et al., "The Hypersensitive Reaction of Tobacco to *Pseudomonas syringae* pv. *pisi,*" *Plant Physiol.*, 79:843–47 (1985).

Huynh et al., "Bacterial Blight of Soybean: Regulation of a Pathogen Gene Determining Host Cultivar Specificity," *Science*, 245:1374–77 (1986).

Kloepper et al., "Plant Growth–Promoting Rhizobacteria on Canola (Rapeseed)," *Plant Disease*, 72(1):42–6 (1988).

Kloepper et al., "Enhanced Plant Growth by Siderophores Produced by Plant Growth–Promoting Rhizobacteria," *Nature*, 286:885–86 (1980).

Kloepper et al., "Pseudomonas Siderophores: A Mechanism Explaining Disease–Suppressive Soils," *Current Microbiology*, 4:317–20 (1980).

Kloepper et al., "Emergence–Promoting Rhizobacteria: Description and Implications for Agriculture," In: *Iron, Siderophores, and Plant Disease*, Swinborne (ed), Plenum, NY, 155–64 (1986).

Kloepper et al., "Relationships of in vitro Antibiosis of Plant Growth–Promoting Rhizobacteria to Plant Growth and the Displacement of Root Microflora," *Phytopathology*, 71(10):1020–24 (1981).

Kloepper et al., "Effects of Rhizosphere Colonization by Plant Growth–Promoting Rhizobacteria on Potato Plant Development and Yield," *Phytopathology*, 70(11):1078–82 (1980).

Kloepper et al., "Plant Growth Promotion Mediated by Rhizosphere Bacterial Colonizers," In: *The Rhizosphere and Plant Growth*,—315–32, Keister et al. (eds), pp. 315–326 (1991).

Lifshitz et al., "Growth Promotion of Canola (rapeseed) Seedlings by a Strain of *Pseudomonas putida* Under Gnotobiotic Conditions," Conditions, *Microbiol.* 33:390–95 (1987).

Liu et al., "Induction of Systemic Resistance in Cucumber Against Bacterial Angular Leaf Spot by Plant Growth–Promoting Rhizobacteria," *Phytopathology*, 85(8):843–47 (1995).

Loper et al., "Influence of Bacterial Sources of Indole–3–acetic Acid on Root Elongation of Sugar Beet," *Phytopathology*, 76(4):386–89 (1986).

Schroth et al., "Disease–Suppressive Soil and Root–Colonizing Bacteria," *Science*, 216:1376–81 (1982).

Stutz et al., "Naturally Occurring Fluorescent Pseudomonads Involved Suppression of Black Root Rot of Tobacco," *Phytopathology*, 76(2):181–85 (1986).

Lindgren et al., "Gene Cluster of *Pseudomonas syringae* pv. "*phaseolicola*" Controls Pathogenicity of Bean Plants and Hypersensitivity on Nonhost Plants," *J. Bacteriol.*, 168(2):512–22 (1986).

Bauer et al., "Cloning of a Gene from *Erwinia amylovora* Involved in Induction of Hypersensitivity and Pathogenicity," *Plant Pathogenic Bacteria*, Proceedings of the Sixth International Conference on Plant Pathogenic Bacteria, Maryland, pp. 425–429 (1987).

Wei et al., "Introduction of Systemic Resistance of Cucumber to *Colletotrichum orbiculare* by Select Strains of Plant Growth–Promoting Rhizobacteria," *Phytopathology*, 81:1508–12 (1991).

Wei et al., "Induction of Systemic Resistance with Seed Treatment by PGPR Strains," pp. 191–194.

Weller, D.M., "Biological Control of Soilborne Plant Pathogens in the Rhizosphere with Bacteria," *Ann. Rev. Phytopathol.*, 26:379–407 (1988).

Young et al., "PGPR: Is There A Relationship Between Plant Growth Regulators and the Stimulation of Plant Growth or Biological Activity?," pp. 182–186.

Wei et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–70 (1987).

Malamy et al., "Salicylic Acid: A Likely Endogenous Signal in the Resistance Response of Tobacco to Viral Infection," *Science*, 250:1002–04 (1990).

Dean et al., "Immunisation Against Disease: The Plant Fights Back," pp. 383–411.

Cameron et al., "Biologically Induced Systemic Acquired Resistance in *Aradibopsis thaliana,*" *The Plant Journal*, 5(5):715–25 (1994).

Laby et al., "Structural and Functional Analysis of *Erwinia amylovora* Harpin, An Elicitor of the Plant Hypersensitive Response," *Phytopathology*, 84:345 (1994).

Van Gijsegem et al., "Evolutionary Conservation of Pathogenicity Determinants Among Plant and Animal Pathogenic Bacteria," *Trends Micorbiol.*, 1:175–80 (1993).

Kamoun, et al., "Extracellular Protein Elicitors from Phytophthora: Host–Specificity and Induction of Resistance to Bacterial and Fungal Phytopathogens," *Molecular Plant–Microbe Interactions*, 6(1):15–25 (1993).

Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal*, 8(4):551–60 (1995).

Collinge et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli,*" *Methods in Enzymology*, 152:661–73 (1987).

Tenhaken, et al., "Function of the Oxidative Burst in Hypersensitive Disease Resistance," *Proc. Natl. Acad. Sci. USA*, 92:4158–63 (1995).

Bonnet, et al., "Induction de nécroses foliaires, de protéines b et de résistance dans les interactions tabac Phytophthora," *Agronomie*, 6(9):829–37 (1986).

Gallitelli, et al., "Satellite–Mediated Protection of Tomato Against Cucumber Mosaic Virus: II. Field Test Under Natural Epidemic Conditions in Southern Italy," *Plant Disease*, 75(1):93–5 (1991).

Kang et al., "Control of Tomato Mosaic Disease by Interference of an Attenuated Virus," *Res. Rept. RDA (Hort.)*, 27(1):17–26 (1985).

Montasser, et al., "Satellite–Mediated Protection of Tomato Against Cucumber Mosaic Virus: I. Greenhouse Experiments and Simulated Epidemic Conditions in the Field," *Plant Disease*, 75(1):86–92 (1991).

Marks, R.J., "Varietal Resistance to Potato Cyst Nematode," *Agricultural Entomology*, pp. 63–67 (1979).

Walton, et al., "Host–Selective Toxins and Disease Specificity: Perspectives and Progress," *Annu. Rev. Phytopathol.*, 31:275–303 (1993).

Atkinson, M.M., "Molecular Mechanisms of Pathogen Recognition by Plants," *Advances in Plant Pathology*, 10:36–64 (1993).

Godiard, et al., "Differential Regulation in Tobacco Cell Suspensions of Genes Involved in Plant–Bacteria Interactions by Pathogen–Related Signals," *Plant Molecular Biology*, 17:409–13 (1991).

Ricci, et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova, I.T., "Induction of Plant Resistance to Viral Diseases: Application of Vaccination," *Sel'skokhozyaistvennaya Biologiya, Biologiya* 3:39–51 (1991).

*Biologicheskii Zhurnal Armenii*, 31(3):305–09 (1978).

Lakhmatova, I.T., "Using Biologically Active Substances to Induced Plant Resistance to Viruses Immunization," *Sel'skokhozyaistvennaya Biologiya*, 3:13–22 (1992).

Shields, R., "Towards Insect–Resistant Plants," *Nature*, 328:12–13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10):4748–56 (1988).

Ricci, et al., "Differential Production of Parasiticein, an Elicitor of Necrosis and Resistance in Tobacco, by Isolates of *Phytophthora parasitica,*" *Plant Patholoyg*, 41:298–307 (1992).

Honée, et al., "Molecular Characterization of the Interaction Between the Fungal Pathogen *Cladosporium fulvum* and Tomato," *Advances in Molecular Genetics of Plant–Microbe Interactions*, 3:199–206 (1994).

Keller, et al., "Response of Tobacco to Elicitins, Proteins From *Phytophthora spp.* Eliciting Acquired Resistance," *Advances in Molecular Genetics of Plant–Microbe Interactions*, 3:327–32 (1994).

Keen, et al., "Bacteria Expressing Avirulence Gene D Produce a Specific Elicitor of the Soybean Hypersensitive Reaction," *Molecular Plant–Microbe Interactions*, 3(2):112–21 (1990).

Bauer, et al., "*Erwinia chrysanthemi hrp* Genes and Their Involvement in Soft Rot Pathogenesis and Elicitation of the Hypersensitive Response," *MPMI*, 7(5):573–81 (1994).

Schottens–Toma et al., "Purification and Primary Structure of a Necrosis–inducing Peptide from the Apoplastic Fluids of Tomato Infected with *Cladosporium fulvum* (syn. *Fulvia fulva*)," *Physiological and Molecular Plant Pathology*, 33:59–67 (1988).

Steinberger et al., "Creation and Complementation of Pathogenicity Mutants of *Erwinia amylovora*," *Molecular Plant–Microbe Interactions*, 1(3):135–44 (1988).

Beer et al., "The Hypersensitive Response is Elicited by *Escherichia coli* Containing a Cluster of Pathogenicity Genes from *Erwinia amylovora*," *Phytopathology*, 79(10):1156 (Abstract 169) (1989).

Hiatt et al., "Production of Antibodies in Transgenic Plants," *Nature*, 342:76–8 (1989).

Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230–34(1989).

Huang et al., "Isolation and Purification of a Factor from *Pseudomonas solanacearum* That Induces a Hypersensitive–like Response in Potato Cells," *Molecular Plant–Microbe Interactions*, 2(3):132–38 (1989).

James et al., "Genetic Transformation of Apple (*Malus pumila* Mill.) Using a Disarmed Ti–binary Vector," *Plant Cell Reports*, 7:658–61 (1989).

Laby et al., "Cloning and Preliminary Characterization of an hrp Gene Cluster of *Erwinia amylovora," Phytopathology*, 79(10):1211 (Abstract 607) (1989).

Dow et al., "Extracellular Proteases from *Xanthomonas campestris* pv. *campestris*, the Black Rot Pathogen," *Applied and Environmental Microbiology*, 56(10):2994–98 (1990).

Walters et al., "Gene for Pathogenicity and Ability to Cause the Hypersensitive Reaction Cloned from *Erwinia amylovora," Physiological and Molecular Plant Pathology*, 36:509–21 (1990).

Wu et al., "Cloning, Genetic Organization, and Characerization of a Structural Gene Encoding Bacillopeptidase F from *Bacillus subtilis," The Journal of Biological Chemistry*, 265(12):6845–50 (1990).

Bauer et al., "Further Characterization of an hrp Gene Cluster of *Erwinia amylovora," Molecular Plant–Microbe Interactions*, 4(5):493–99 (1991).

Beer et al., "The hrp Gene Cluster of *Erwinia amylovora," Advances in Molecular Genetics of Plant–Microbe Interactions*, 1:53–60 (1991).

Benvenuto et al., "'Phytoantibodies': A General Vector for the Expression of Immunoglobulin Domains in Transgenic Plants," *Plant Molecular Biology*, 17:865–74 (1991).

Milat et al., "Physiological and Structural Changes in Tobacco Leaves Treated with Cryptogein, a Proteinaceous Elicitor from *Phytophthora cryptogea," Phytopathology*, 81(11):1364–68 (1991).

Ruberti et al., "A Novel Class of Plant Proteins Containing a Homeodomain with a Closely Linked Leucine Zipper Motif," *The EMBO Journal*, 10(7):1787–91 (1991).

Quigley et al., "Nucleotide Sequence and Expression of a Novel Glycine–Rich Protein Gene from *Arabidopsis thaliana," Plant Molecular Biology*, 17:949–52 (1991).

van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–9 (1991).

Waldmann, T.A., "Monoclonal Antibodies in Diagnosis and Therapy,"*Science*, 252:1657–62 (1991).

Willis et al., "hrp Genes of Phytopathogenic Bacteria," *Molecular Plant–Microbe Interactions*, 4:(2) 132–38 (1991).

Beer et al., "Are Harpins Universal Elicitors of the Hypersensitive Response of Phytopathogenic Bacteria?," *Advances in Molecular Genetics of Plant–Microbe Interactions*, 2:281–86 (1992).

Laby et al., "Hybridization and Functional Complementation of the hrp Gene Cluster from *Erwinia amylovora* Strain Ea321 with DNA of Other Bacteria," *Molecular Plant–Microbe Interactions*, 5(5):412–19 (1992).

Sandhu, "Protein Engineering of Antibodies," *Crit. Rev. in Biotech.*, 12(5/6):437–62 (1992).

Wei et al., "Harpin, Elicitor of the Hypersensitive Response Produced by the Plant Pathogen *Erwinia amylovora," Science*, 257:85–8 (1992).

He et al., "*Pseudomonas syringae* pv. *syringae* Harpin$_{Pss}$: A Protein that is Secreted via the Hrp Pathway and Elicits the Hypersensitive Response in Plants," *Cell*, 73:1255–66 (1993).

Bonas, U., "Bacterial Home Goal by Harpins," *Trends in Microbiology*, 2:1–2 (1994).
Boccara, et al., "Plant Defense Elicitor Protein Produced by *Erwinia chrysanthemi,*" *Mechanisms of Plant Defense Responses*, p. 166 (1993).
Qui et al., "Treatment of Tomato Seed with Harpin Enhances Germination and Growth and Induces Resistance to *Ralstonia solanacearum,*" *Phytopathology*, 87:6, S80 (1997).
Burr et al., "Increased Potato Yields by Treatment of Seedpieces with Specific Strains of *Pseudomonas fluorescens* and *P. putida,*" *Phytopathology*, 68:1377–1383 (1978).
Ricci et al., "Proteinaceous Elicitors of Plant Defense Responses," B. Fritig eds., *Mechanisms of Plant Defense Responses*, Netherlands, pp. 121–130 (1993).
Keen et al., "Syringolide Elicitors Specified By Avirulence Gene D Alleles In *Pseudomonas syringae,*" *Advances in Molecular Genetics of Plant–Microbe Interactions*, 3:41–48 (1994).
Klessig et al., "The Salicylic Acid Signal In Plants," *Plant Molecular Biology*, 26:1439–1458 (1994).
Bogdanove et al., "Unified Nomenclature For Broadly Conserved hrp Genes of Phytopathogenic Bacteria," *Molecular Microbiology*, 20(3):681–683 (1996).
Bonnet et al., "Acquired Resistance Triggered By Elicitins In Tobacco and Other Plants," *European Journal of Plant Pathology*, 102:181–192 (1996).
Cui et al., "The RsmA$^{-}$ Mutants of *Erwinia carotovora* subsp. *carotovora* Strain Ecc71 Overexpress hrp$N_{Ecc}$ and Elicit a Hypersensitive Reaction–like Response in Tobacco Leaves," *Molecular Plant–Microbe Interactions*, 9(7):565–573 (1996).
Gopalan et al., "Bacterial Genes Involved in the Elicitation of Hypersensitive Response and Pathogenesis," *Plant Disease*, 80(6):604–610 (1996).

Hoffland et al., "Comparison of Systemic Resistance Induced by Avirulent and Nonpathogenic Pseudomonas Species," *Phytopathology*, 86(7):757–762 (1996).

Ryals et al., "Systemic Acquired Resistance," *The Plant Cell*, 8:1809–1819 (1996).

Wei et al., "Induced Systemic Resistance to Cucumber Dieseases and Increased Plant Growth by Plant Growth–Promoting Rhizobacteria Under Field Conditions," *Phytopathology*, 86:221–224 (1996).

Wengelnik et al., "Expression and Localization of HrpA1, a Protein of *Xanthomonas compestris* pv. vesicatoria Essential for Pathogenicity and Induction of the Hypersensitive Reaction," *Journal of Bacteriology*, 178:1061–1069 (1996).

Inbar et al., "Elicitors of Plant Defensive Systems Reduce Insect Densities and Disease Incidence," *Journal of Chemical Ecology*, 24(1):135–149 (1998).

Jin et al., "A Truncated Fragment of Harpin$_{Pss}$ Induces Systemic Resistance to *Xanthomonas campetris* pv. *oryzae* In Rice," *Physiological and Molecular Plant Pathology*, 51:243–257 (1997).

* cited by examiner

HYPERSENSITIVE RESPONSE ELICITOR FROM *ERWINIA AMYLOVORA* AND ITS USE

This application claims benefit of U.S. Provisional Patent Application Ser. No. 60/055,108, filed Aug. 6, 1997.

FIELD OF THE INVENTION

The present invention relates to a hypersensitive response elicitor from *Erwinia amylovora* and its use.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phytopathogenic Prokaryotes*, Vol. 2, M. S. Mount and G. H. Lacy, ed. Academic Press, New York (1982)). The hypersensitive response elicited by bacteria is readily observed as a tissue collapse if high concentrations ($\geqq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199:299–300; Klement, et al., "Hypersensitive Reaction Induced by Phytopathogenic Bacteria in the Tobacco Leaf," *Phytopathology* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in Phytopathogenic Prokaryotes, Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in Phytopathogenic Prokaryotes, Vol. 2., M. S. Mount and G. H. Lacy, ed. Academic Press, New York, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in gram-negative plant pathogens, where they are clustered, conserved, and in some cases interchangeable (Willis, D. K., et al., "hrp Genes of Phytopathogenic Bacteria," *Mol. Plant-Microbe Interact.* 4:132–138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms*, J. L. Dangl, ed. Springer-Verlag, Berlin (1994)). Several hrp genes encode components of a protein secretion pathway similar to one used by *Yersinia, Shigella*, and *Salmonella* spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993)). In *E. amylovora, P. syringae*, and *P. solanacearum*, hrp genes have been shown to control the production and secretion of glycine-rich, protein elicitors of the hypersensitive response (He, S. Y., et al. "Pseudomonas Syringae pv. Syringae HarpinPss: a Protein that is Secreted via the Hrp Pathway and Elicits the Hypersensitive Response in Plants," *Cell* 73:1255–1266 (1993), Wei, Z. —H., et al., "HrpI of *Erwinia amylovora* Functions in Secretion of Harpin and is a Member of a New Protein Family," *J. Bacteriol.* 175:7958–7967 (1993); Arlat, M. et al. "PopA1, a Protein Which Induces a Hypersensitive-like Response on Specific Petunia Genotypes, is Secreted via the Hrp Pathway of *Pseudomonas solanacearum," EMBO J.* 13:543–553 (1994)).

The first of these proteins was discovered in *E. amylovora* Ea321, a bacterium that causes fire blight of rosaceous plants, and was designated harpin (Wei, Z. —M., et al, "Harpin, Elicitor of the Hypersensitive Response Produced by the Plant Pathogen *Erwinia amylovora," Science* 257:85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI1000 PopA1 protein has similar physical properties and also elicits the hypersensitive response in leaves of tobacco, which is not a host of that strain (Arlat, et al. "PopA1, a Protein Which Induces a Hypersensitive-like Response on Specific Petunia Genotypes, is Secreted via the Hrp Pathway of *Pseudomonas solanacearum," EMBO J.* 13:543–53 (1994)). However, *P. solanacearum popA* mutants still elicit the hypersensitive response in tobacco and incite disease in tomato. Thus, the role of these glycine-rich hypersensitive response elicitors can vary widely among gram-negative plant pathogens.

Other plant pathogenic hypersensitive response elicitors have been isolated, cloned, and sequenced. These include: *Erwinia chrysanthemi* (Bauer, et. al., *"Erwinia chrysanthemi* Harpin$_{Ech}$: Soft-Rot Pathogenesis," *MPMI* 8(4) :484–91 (1995)); *Erwinia carotovora* (Cui, et. al., "The RsmA$^-$ Mutants of *Erwinia carotovora* subsp. *carotovora* Strain Ecc71 Overexpress hrpN$_{Ecc}$ and Elicit a Hypersensitive Reaction-like Response in Tobacco Leaves," *MPMI* 9(7): 565–73 (1966)); *Erwinia stewartii* (Ahmad, et. al., "Harpin is not Necessary for the Pathogenicity of *Erwinia stewartii* on Maize," 8th Int'l. Cong. Molec. Plant-Microb. Inter. Jul. 14–19, 1996 and Ahmad, et. al., "Harpin is not Necessary for the Pathogenicity of *Erwinia stewartii* on Maize," *Ann. Mtg. Am. Phytopath. Soc.* Jul. 27–31, 1996); and *Pseudomonas syringae* pv. *syringae* (WO 94/26782 to Cornell Research Foundation, Inc.).

The present invention is a further advance in the effort to identify, clone, and sequence hypersensitive response elicitor proteins or polypeptides from plant pathogens.

SUMMARY OF THE INVENTION

The present invention is directed to an isolated protein or polypeptide which elicits a hypersensitive response in plants as well as an isolated DNA molecule which encodes the hypersensitive response eliciting protein or polypeptide.

The hypersensitive response eliciting protein or polypeptide can be used to impart disease resistance to plants, to enhance plant growth, and/or to control insects. This involves applying the hypersensitive response elicitor protein or polypeptide in a non-infectious form to plants or plant seeds under conditions effective to impart disease resistance, to enhance plant growth, and/or to control insects on plants or plants grown from the plant seeds.

As an alternative to applying the hypersensitive response elicitor protein or polypeptide to plants or plant seeds in order to impart disease resistance, to enhance plant growth, and/or to control insects on plants, transgenic plants or plant seeds can be utilized. When utilizing transgenic plants, this involves providing a transgenic plant transformed with a DNA molecule encoding a hypersensitive response elicitor protein or polypeptide and growing the plant under conditions effective to impart disease resistance, to enhance plant growth, and/or to control insects in the plants or plants grown from the plant seeds. Alternatively, a transgenic plant seed transformed with the DNA molecule encoding a hypersensitive response elicitor protein or polypeptide can be provided and planted in soil. A plant is then propagated under conditions effective to impart disease resistance, to enhance plant growth, and/or to control insects on plants or plants grown from the plant seeds.

BRIEF DESCRIPTION OF THE DRAWINGS

FIG. 1A depicts cosmids pCPP430 and pCPP 450 that contain the regulatory and secretory region of the hrp cluster of *E. amylovora*. Arrow boxes on top of the cosmid clones indicate the transcriptional units, where the names of the characterized operons are given above (Wei, et al., *Science,* 257:85–88 (1992); Zumoff, et al., *The hrp Gene Cluster of Erwinia amylovora*, eds. Hennecke, H. & Verna, D. P. S. (Kluwer Academic Publishers, Dordrecht, The Netherlands), Vol. 1, pp. 53–60 (1991); Bogdanove, et al., *J. Bacteriol.,* 178:1720–30 (1996); and Kim, et al., *J. Bacteriol.,* 179:1690–97 (1997), which are hereby incorporated by reference).

DETAILED DESCRIPTION OF THE INVENTION

Figure 1A:
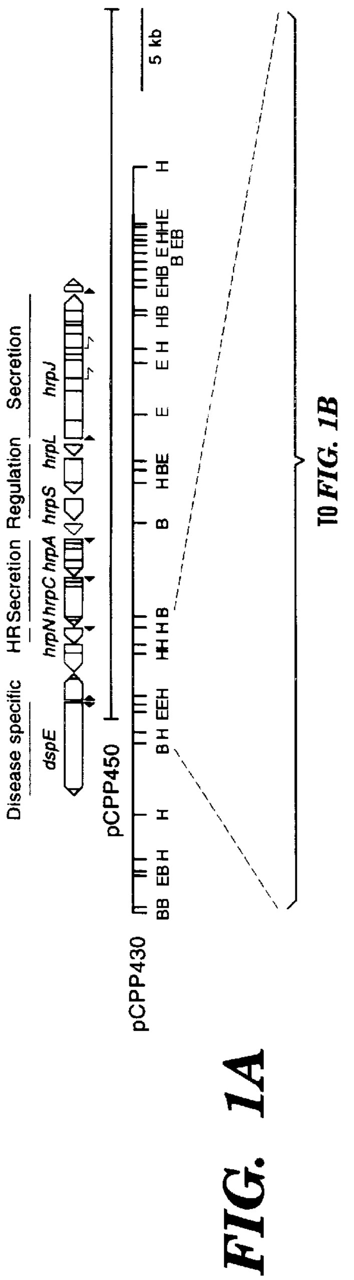
FIGS. 1A and B show the molecular structure of the region of *E. amylovora* genome containing hrpW.

The present invention relates to an isolated DNA molecule having a nucleotide sequence of SEQ. ID. No. 1 as follows:

```
ATGTCAATTC TTACGCTTAA CAACAATACC TCGTCCTCGC CGGGTCTGTT CCAGTCCGGG    60

GGGGACAACG GGCTTGGTGG TCATAATGCA AATTCTGCGT TGGGGCAACA ACCCATCGAT   120

CGGCAAACCA TTGAGCAAAT GGCTCAATTA TTGGCGGAAC TGTTAAAGTC ACTGCTATCG   160

CCACAATCAG GTAATGCGGC AACCGGAGCC GGTGGCAATG ACCAGACTAC AGGAGTTGGT   240

AACGCTGGCG GCCTGAACGG ACGAAAAGGC ACAGCAGGAA CCACTCCGCA GTCTGACAGT   300
```

-continued

```
CAGAACATGC TGAGTGAGAT GGGCAACAAC GGGCTGGATC AGGCCATCAC GCCCGATGGC   360
CAGGGCGGCG GGCAGATCGG CGATAATCCT TTACTGAAAG CCATGCTGAA GCTTATTGCA   420
CGCATGATGG ACGGCCAAAG CGATCAGTTT GGCCAACCTG GTACGGGCAA CAACAGTGCC   480
TCTTCCGGTA CTTCTTCATC TGGCGGTTCC CCTTTTAACG ATCTATCAGG GGGGAAGGCC   540
CCTTCCGGCA ACTCCCCTTC CGGCAACTAC TCTCCCGTCA GTACCTTCTC ACCCCCATCC   600
ACGCCAACGT CCCCTACCTC ACCGCTTGAT TTCCCTTCTT CTCCCACCAA AGCAGCCGGG   660
GGCAGCACGC CGGTAACCGA TCATCCTGAC CCTGTTGGTA GCGCGGGCAT CGGGGCCGGA   720
AATTCGGTGG CCTTCACCAG CGCCGGCGCT AATCAGACGG TGCTGCATGA CACCATTACC   780
GTGAAAGCGG GTCAGGTGTT TGATGGCAAA GGACAAACCT TCACCGCCGG TTCAGAATTA   840
GGCGATGGCG GCCAGTCTGA AAACCAGAAA CCGCTGTTTA TACTGGAAGA CGGTGCCAGC   900
CTGAAAAACG TCACCATGGG CGACGACGGG GCGGATGGTA TTCATCTTTA CGGTGATGCC   960
AAAATAGACA ATCTGCACGT CACCAACGTG GGTGAGGACG CGATTACCGT TAAGCCAAAC  1020
AGCGCGGGCA AAAAATCCCA CGTTGAAATC ACTAACAGTT CCTTCGAGCA CGCCTCTGAC  1080
AAGATCCTGC AGCTGAATGC CGATACTAAC CTGAGCGTTG ACAACGTGAA GGCCAAAGAC  1140
TTTGGTACTT TTGTACGCAC TAACGGCGGT CAACAGGGTA ACTGGGATCT GAATCTGAGC  1200
CATATCAGCG CAGAAGACGG TAAGTTCTCG TTCGTTAAAA GCGATAGCGA GGGGCTAAAC  1260
GTCAATACCA GTGATATCTC ACTGGGTGAT GTTGAAAACC ACTACAAAGT GCCGATGTCC  1320
GCCAACCTGA AGGTGGCTGA ATGA                                         1344
```

See GenBank Accession No. U94513. The isolated DNA molecule of the present invention encodes a hypersensitive response elicitor protein or polypeptide having an amino acid sequence of SEQ. ID. No. 2 as follows:

```
Met Ser Ile Leu Thr Leu Asn Asn Asn Thr Ser Ser Ser Pro Gly Leu
1               5                   10                  15

Phe Gln Ser Gly Gly Asp Asn Gly Leu Gly Gly His Asn Ala Asn Ser
            20                  25                  30

Ala Leu Gly Gln Gln Pro Ile Asp Arg Gln Thr Ile Glu Gln Met Ala
        35                  40                  45

Gln Leu Leu Ala Glu Leu Leu Lys Ser Leu Leu Ser Pro Gln Ser Gly
    50                  55                  60

Asn Ala Ala Thr Gly Ala Gly Gly Asn Asp Gln Thr Thr Gly Val Gly
65                  70                  75                  80

Asn Ala Gly Gly Leu Asn Gly Arg Lys Gly Thr Ala Gly Thr Thr Pro
                85                  90                  95

Gln Ser Asp Ser Gln Asn Met Leu Ser Glu Met Gly Asn Asn Gly Leu
            100                 105                 110

Asp Gln Ala Ile Thr Pro Asp Gly Gln Gly Gly Gly Gln Ile Gly Asp
        115                 120                 125

Asn Pro Leu Leu Lys Ala Met Leu Lys Leu Ile Ala Arg Met Met Asp
    130                 135                 140

Gly Gln Ser Asp Gln Phe Gly Gln Pro Gly Thr Gly Asn Asn Ser Ala
145                 150                 155                 160

Ser Ser Gly Thr Ser Ser Ser Gly Gly Ser Pro Phe Asn Asp Leu Ser
                165                 170                 175

Gly Gly Lys Ala Pro Ser Gly Asn Ser Pro Ser Gly Asn Tyr Ser Pro
```

-continued

```
        180                     185                     190

Val Ser Thr Phe Ser Pro Pro Ser Thr Pro Thr Ser Pro Thr Ser Pro
            195                 200                 205

Leu Asp Phe Pro Ser Ser Pro Thr Lys Ala Ala Gly Gly Ser Thr Pro
    210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
                245                 250                 255

Asp Thr Ile Thr Val Lys Ala Gly Gln Val Phe Asp Gly Lys Gly Gln
            260                 265                 270

Thr Phe Thr Ala Gly Ser Glu Leu Gly Asp Gly Gly Gln Ser Glu Asn
        275                 280                 285

Gln Lys Pro Leu Phe Ile Leu Glu Asp Gly Ala Ser Leu Lys Asn Val
    290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
                325                 330                 335

Val Lys Pro Asn Ser Ala Gly Lys Lys Ser His Val Glu Ile Thr Asn
            340                 345                 350

Ser Ser Phe Glu His Ala Ser Asp Lys Ile Leu Gln Leu Asn Ala Asp
        355                 360                 365

Thr Asn Leu Ser Val Asp Asn Val Lys Ala Lys Asp Phe Gly Thr Phe
    370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
            420                 425                 430

Asn His Tyr Lys Val Pro Met Ser Ala Asn Leu Lys Val Ala Glu
        435                 440                 445
```

This protein or polypeptide is acidic, rich in glycine and serine, and lacks cysteine. It is also heat stable, protease sensitive, and suppressed by inhibitors of plant metabolism. The protein or polypeptide of the present invention has a predicted molecular size of ca. 4.5 kDa.

Fragments of the above hypersensitive response elicitor polypeptide or protein are encompassed by the the present invention.

Suitable fragments can be produced by several means. In the first, subclones of the gene encoding the elicitor protein of the present invention are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or *Staphylococcus* proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of SEQ. ID. No. 1 under stringent conditions. An example of suitable stringency conditions is when hybridization is carried out at 65° C. for 20 hours in a medium containing 1 M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 μm g/ml E. coli DNA. However, any DNA molecules hybridizing to a DNA molecule comprising the nucleotide sequence of SEQ. ID. No. 1 under such stringent conditions must not be identical to the nucleic acids encoding the hypersensitive response elicitor proteins or polypeptides of E. amylovora (as disclosed by Wei, Z. —M., et al, "Harpin, Elicitor of the Hypersensitive Response Produced by the Plant Pathogen Erwinia amylovora," Science 257:85–88 (1992), which is hereby incorporated by reference), Erwinia chrysanthemi (as disclosed by Bauer, et. al., "Erwinia chrysanthemi $Harpin_{Ech}$: Soft-Rot Pathogenesis," MPMI 8(4): 484–91 (1995), which is hereby incorporated by reference), Erwinia carotovora (as disclosed by Cui, et. al., "The RsmA⁻ Mutants of Erwinia carotovora subsp. carotovora Strain Ecc71 Overexpress $hrpN_{Ecc}$ and Elicit a Hypersensitive Reaction-like Response in Tobacco Leaves," MPMI 9(7): 565–73 (1966), which is hereby incorporated by reference), Erwinia stewartii (as disclosed by Ahmad, et. al., "Harpin is not Necessary for the Pathogenicity of Erwinia stewartii on Maize," 8th Int'l. Cong. Molec. Plant-Microb. Inter. Jul. 14–19, 1996 and Ahmad, et. al., "Harpin is not Necessary for the Pathogenicity of Erwinia stewartii on Maize," Ann. Mtg. Am. Phytopath. Soc. Jul. 27–31, 1996), which are hereby incorporated by reference), and Pseudomonas syringae pv. syringae (WO 94/26782 to Cornell Research Foundation, Inc., which is hereby incorporated by reference).

The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell (e.g., E. coli) carrying a recombinant plasmid is propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/– or KS +/– (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," Gene Expression Technology vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., Molecular Cloning: A Laboratory Manual, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promotors. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgamo ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, Methods in Enzymology, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention further relates to methods of imparting disease resistance to plants, enhancing plant growth, and/or effecting insect control for plants. These methods involve applying a hypersensitive response elicitor polypeptide or protein in a non-infectious form to all or part of a plant or a plant seed under conditions where the polypeptide or protein contacts all or part of the cells of the plant or plant seed. Alternatively, the hypersensitive response elicitor protein or polypeptide can be applied to plants such that seeds recovered from such plants themselves are able to impart disease resistance in plants, to enhance plant growth, and/or to effect insect control.

As an alternative to applying a hypersensitive response elicitor polypeptide or protein to plants or plant seeds in order to impart disease resistance in plants, to effect plant growth, and/or to control insects on the plants or plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to impart disease resistance to plants, to enhance plant growth, and/or to control insects. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to impart disease resistance to plants, to enhance plant growth, and/or to control insects.

The embodiment of the present invention where the hypersensitive response elicitor polypeptide or protein is applied to the plant or plant seed can be carried out in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein.

In one embodiment of the present invention, the hypersensitive response elicitor polypeptide or protein of the present invention can be isolated from *Erwinia amylovora* as described in Examples infra. Preferably, however, the isolated hypersensitive response elicitor polypeptide or protein of the present invention is produced recombinantly and purified as described supra.

In other embodiments of the present invention, the hypersensitive response elicitor polypeptide or protein of the present invention can be applied to plants or plant seeds by applying bacteria containing genes encoding the hypersensitive response elicitor polypeptide or protein. Such bacteria must be capable of secreting or exporting the polypeptide or protein so that the elicitor can contact plant or plant seeds cells. In these embodiments, the hypersensitive response elicitor polypeptide or protein is produced by the bacteria in planta or on seeds or just prior to introduction of the bacteria to the plants or plant seeds.

In one embodiment of the bacterial application mode of the present invention, the bacteria do not cause the disease and have been transformed (e.g., recombinantly) with genes encoding a hypersensitive response elicitor polypeptide or protein. For example, *E. coli*, which does not elicit a hypersensitive response in plants, can be transformed with genes encoding a hypersensitive response elicitor polypeptide or protein and then applied to plants. Bacterial species other than *E. coli* can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment, these bacteria are applied to plants or their seeds which are not susceptible to the disease carried by the bacteria. For example, *Erwinia amylovora* causes disease in apple or pear but not in tomato. However, such bacteria will elicit a hypersensitive response in tomato. Accordingly, in accordance with this embodiment of the present invention, *Erwinia amylovora* can be applied to tomato plants or seeds to impart disease resistance, enhance growth, or control insects without causing disease in that species.

The method of the present invention can be utilized to treat a wide variety of plants or their seeds to impart disease resistance, enhance growth, and/or control insects. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana, Saintpaulia*, petunia, pelargonium, poinsettia, chrysanthemum, carnation, and zinnia.

With regard to the use of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fimgal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: *Tobacco mosaic virus* and *Tomato mosaic virus*. Resistance, inter alia, to the following bacteria can also be imparted to plants in accordance with present invention: *Pseudomonas solancearum, Pseudomonas syringae* pv. *tabaci*, and *Xanthamonas campestris* pv. *pelargonii*. Plants can be made resistant, inter alia, to the following fungi by use of the method of the present invention: *Fusarium oxysporum* and *Phytophthora infestans*.

With regard to the use of the hypersensitive response elicitor protein or polypeptide of the present invention to enhance plant growth, various forms of plant growth enhancement or promotion can be achieved. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Another aspect of the present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection.

The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide.

The method of the present invention involving application of the hypersensitive response elicitor polypeptide or protein can be carried out through a variety of procedures when all or part of the plant is treated, including leaves, stems, roots, propagules (e.g., cuttings), etc. This may (but need not) involve infiltration of the hypersensitive response elicitor polypeptide or protein into the plant. Suitable application methods include high or low pressure spraying, injection, and leaf abrasion proximate to when elicitor application takes place. When treating plant seeds, in accordance with the application embodiment of the present invention, the hypersensitive response elicitor protein or polypeptide can be applied by low or high pressure spraying, coating, immersion, or injection. Other suitable application procedures can be envisioned by those skilled in the art provided they are able to effect contact of the hypersensitive response elicitor polypeptide or protein with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to impart disease resistance to plants, to enhance plant growth, and/or to control insects on the plants.

The hypersensitive response elicitor polypeptide or protein can be applied to plants or plant seeds in accordance with the present invention alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. In this embodiment, the composition contains greater than 500 nM hypersensitive response elicitor polypeptide or protein.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

In the alternative embodiment of the present invention involving the use of transgenic plants and transgenic seeds, a hypersensitive response elicitor polypeptide or protein need not be applied topically to the plants or seeds. Instead, transgenic plants transformed with a DNA molecule encoding a hypersensitive response elicitor polypeptide or protein are produced according to procedures well known in the art.

The vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA*, 79:1859–63 (1982), which is hereby incorporated by reference.

The DNA molecule may also be introduced into the plant cells by electroporation. Fromm et al., *Proc. Natl. Acad. Sci. USA*, 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures*, Vol. 1: (MacMillan Publishing Co., New York, 1983); and Vasil I. R. (ed.), *Cell Culture and Somatic Cell Genetics of Plants*, Acad. Press, Orlando, Vol. 1, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in disease resistance, enhanced plant growth, and/or control of insects on the plant. Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart disease resistance to plants, to enhance plant growth, and/or to control insects. While not wishing to be bound by theory, such disease resistance, growth enhancement, and/or insect control may be RNA mediated or may result from expression of the elicitor polypeptide or protein.

When transgenic plants and plant seeds are used in accordance with the present invention, they additionally can be treated with the same materials as are used to treat the plants and seeds to which a hypersensitive response elicitor polypeptide or protein is applied. These other materials, including hypersensitive response elicitors, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the hypersensitive response elicitor to impart disease resistance, enhance growth, and/or control insects. Such plants may also be treated with conventional plant treatment agents (e.g., insecticides, fertilizers, etc.).

EXAMPLES

Example 1—Bacterial Strains and Plasmids

*E. amylovora* Ea321 and Ea273 are wild-type strains that infect pomaceous plants (Beer et al., *The hrp Gene Cluster of Erwinia amylovora*, eds. Hennecke, H. & Verma, D. P. S. (Kluwer Academic Publishers, Dordrecht, The Netherlands), Vol. 1, pp. 53–50 (1991), which is hereby incorporated by reference). *Escherichia coli* DH5α was used routinely as the host of plasmids. pCPP1012 is a subclone of pCPP430, and pCPP1152, pCPP1218, pCPP1219 and pCPP1220 were constructed by cloning restriction fragments of pCPP1012 into pBluescript KS (+) (Stratagene, La Jolla, Calif.) (FIG. 1B). pCPP1227 was cloned from pCPP 1220 into the same vector.

Example 2—Molecular Biological Techniques and Sequence Analysis.

General molecular procedures were performed using standard techniques as described (Sambrook, et al., *Molecular Cloning: A Laboratory Manual*, (Cold Spring Harbor Laboratory, Cold Spring Harbor, N.Y.) (1989), which is hereby incorporated by reference). Sequencing was done on an ABI 373A automated DNA sequencer at the Cornell University Biotechnology Program DNA Sequencing Facility. For DNA and protein sequence analyses, programs in the GCG software package, Version 7.3 (Genetics Computer Group, Inc., Madison, Wis.) and DNASTAR (DNASTAR, Inc., Madison, Wis.) were used.

Example 3—Expression of hrpW in *E. coil.*

The 1.4-kb Hpal fragment of pCPP1227 that contains hrpW was subcloned into pBC SK (–) (Stratagene, La Jolla, Calif.) such that hrpW is under the control of T7Φ10 promoter. The resulting plasmid, pCPP1232 (FIG. 1B), was introduced into *E. coli* DH5α(pGP1-2) (Tabor, et al., *Proc. Natl. Acad. Sci. USA,* 82:1074–78 (1985), which is hereby incorporated by reference). Cells were incubated at 42° C. to induce the expression of the T7 RNA polymerase gene, and newly synthesized proteins were radiolabelled with $^{35}$S-Met as described (Tabor, et al., *Proc. Natl. Acad. Sci. USA,* 82:1074–78 (1985), which is hereby incorporated by reference). Resulting samples were resuspended in a crackling buffer and heated to 95° C. for 3 min before SDS-polyacrylamide gel electrophoresis (SDS-PAGE) in a 10% gel.

Example 4—Purification of HrpW.

HrpW, produced by heat-shock treatment of *E. Coli* DH5α(pGP1-2, pCPP1232) at 42° C., was purified by cutting out the area of the gel containing HrpW, eluting the protein with ELUTRAP (Schleicher & Schuell, Inc., Keene, N H), and desalting the HrpW-containing solution using Centriprep-30 (Amicon, Inc., Beverly, Mass.) and 5 mM potassium phosphate ($KPO_4$) buffer (pH 6.5). Alternatively, heat-induced and 10-fold concentrated *E. coli* DH5α(pGP1-2, pCPP1232) cells were sonicated in the presence of 1 mM phenylmethlsulfonyl fluoride (PMSF), put in a boiling water bath for 10 min, and centrifuged at 17,500 g for 10 min. The supernatant was desalted resulting in a "cell-free elicitor preparation (CFEP)" of HrpW. The CFEP of HrpW was prepared in the same manner from an HrpN overproducer, *E. coli* DH5α(pCPP2139).

Example 5—Immunodetection of HrpW.

Polyclonal antibodies against HrpW were raised at the College of Veterinary Medicine, Cornell University, by injecting ca. 100 μg of HrpW into a rabbit three times at 2–3 wk intervals. The antiserum was collected 2 wk after the final injection and cross-absorbed with heat-treated lysate of *E. coli* DH5α(pGP1-2, pBC SK (–)).

*E. amylovora* Ea321Rp (a rifampicin-resistant derivative of Ea321), Ea321-K49 (hrpL::Tn 10-miniKm) (Wei, et al., *J. Bacteriol.,* 177:6201–10 (1995), which is hereby incorporated by reference), Ea321-G84 (hrcC::Tn5-gusA1) (Kim et al., *J. Bacteriol.,* 179:1690–97 (1997), which is hereby incorporated by reference), Ea273Rp, Ea273-K49, and Ea273-G73 (hrcY::Tn5-gusA1) were grown overnight in Terrific broth, transferred to a hrp minimal medium (Huynh, et al., *Science,* 345:1374–77 (1989), which is hereby incorporated by reference) at 1 H$10^8$ cfu/ml, and incubated at 20° C. until the bacteria grew to 1 H$10^9$ cfu/ml. Cultures were centrifuged at 17,500 g and the pellet was resuspended in a loading buffer. The supernatant was passed through a membrane filter (0.2 μm pore size; Whatman Inc., Fairfield, N.J.) after adding 1 mM PMSF, and concentrated 100-fold using Centricon-10 and Microcon-10 (Amicon, Inc., Beverly, Mass.) at 4° C. Both the cell and supernatant fractions were then subjected to SDS-PAGE in a 10% gel.

Proteins in the gel were transferred to Immobilon-P (Millipore Co., Bedford, Mass.) and western analysis was performed using a system (Sigma, St. Louis, Mo.) composed of Biotin-conjugated anti-rabbit IgG, ExtrAvidin, and BCIP/NBT tablets for strains of Ea273 and *E. coli*, and using the Western-Light Plus system (Tropix, Inc., Bedford, Mass.) for strains of Ea321.

Example 6—Generation of an N-terminal Fragment of HrpW.

pCPP1232 was digested with BamHI and BstEII and the ends of the 4.1-kb fragment were blunted using the Klenow fragment and self-ligated. The resulting plasmid, pCPP1254, which encodes the N-terminal 226 amino acids of HrpW and Ile-His residues derived from the vector sequence, was cloned in *E. coli* DH5α, and then transferred to *E. coli*DH5α (pGP1-2), generating *E. coli* DH5α(pGP1-2, pCPP1254).

Example 7—Plant Assays.

Elicitation of the HR was tested by infiltrating protein or bacterial preparations into the intercellular space of leaves of tobacco (*Nicotiana tabacum L.* 'xanthi') and other plants (Kim, et al., *J. Bacteriol.,* 179:1690–97 (1997), which is hereby incorporated by reference). Cells were grown either in Luria broth (*E. coli* DH5α and MC4100) or a hrp minimal medium (*E. amylovora* Ea321 and Ea321-T5) (Huynh, et al., *Science,* 345:1374–77 (1989), which is hereby incorporated by reference) to 5 H$10^8$ cfu/ml, and resuspended in 5 mM $KPO_4$ buffer (pH 6.5) to 2 H$10^8$ cfu/ml (*E. coli* strains) or 5 H$10^8$ cfu/ml (*E. amylovora* strains). Inhibitors of plant metabolism used included cycloheximide at 100 μM, $LaCl_3$ at 1 mM, and $Na_3VO_4$ at 50 μM.

Example 8—Southern Blotting.

Genomic DNA was digested with EcoRI, electrophoresed on a 0.7% agarose gel, transferred to an Immobilon-N membrane (Millipore Co., Bedford, Mass.), and hybridized with the $^{32}$P-Labelled 1.4 kb-Hpal fragment of pCPP1227 at 65° C. for 24 hr. The membrane was washed twice with a solution of 2 H SCC and 1.0% SDS at 65° C., and washed with 0.1 H SCC until no radioactivity is detected in the wash solution. For low stringency hybridizations, the membrane was incubated at 50° C. and washed with 2 H SCC at 45° C.

Example 9—Pectic Enzyme Assay of HrpW.

Heat-induced *E. coli* DH5α(pGP1-2, pCPP1232) were pelleted, resuspended in one-tenth volume of 5 mM $KPO_4$ buffer (pH 6.5) or 10 mM Tris-HCI (pH 8.5), sonicated on ice, centrifuged, and PL activity of the supernatant was tested. Also, 50-fold concentrated Ea321 culture supernatant was included in the test. Dilute PelE of *Erwinia Chrysanthemi* EC16 in 10 mM Tris-HCI (pH 7.8) was used as a control.

Ten microliters of each preparation was spotted in YC agar plates (Keen, et al., *J. Bacteriol.,* 159:825–31 (1984), which is hereby incorporated by reference) containing either 0.7% polygalaturonic acid (Sigma, St. Louis, Mo.) or 0.7% pectin (88% methoxylated; Sigma, St. Louis, Mo.) at pH 6.5, 8.0 or 9.5, and in pectin semi-solid agar plates (Starr, et al., *J. Clin. Microbiol.,* 6:379–86 (1977), which is hereby incorporated by reference) containing 3% pectin (88% methoxylated) at pH 6.5, 8.0 or 9.5. The plates were incubated at 37° C. for 24 hr, flooded with 1 M $CaCl_2$, and examined for the presence of halo. Viscometric analysis (Bateman, D. F., *Phytopathology,* 53:197–204 (1963), which is hereby incorporated by reference) and a modified thioarbituric acid procedure (Sherwood, R. T., *Phytopathology,* 56:279–86 (1966), which is hereby incorporated by reference) was done using 1% polygalaturonic acid or 1% pectin (68% methoxylated) in 2.5 mM $CaCl_2$ and 100 mM Tris-HCI, pH 9.5 as substrates. Methods supposedly more sensitive than those above, including an isoelectrofocusing gel procedure and spectrophotometry also were tried. Ten microliters of samples was applied onto an overlay gel (Collmer, et al., *J. Bacteriol.,* 161:913–20 (1985), which is hereby incorporated by reference) containing 0.2% pectin (88% methoxylated), 1% agarose, 1.5 mM $CaCl_2$, and 50 mM Tris-HCI (pH 8.8), and wrapped with plastic film. The gel was incubated at 28° C. for 24 hr, flooded with 1% hexadecyltrimethylammonium bromide, and inspected for clearing. To assay PL activity through generation of double bonds, 1.9 ml of a solution of 0.1% pectin (68% methoxylated), 5 mM $CaCl_2$, and 100 mM Tris-HCI at pH 5.5 or 9.5 was mixed with 100 $\mu$l of samples and absorbance changes at 232 nm was recorded for 30 min as described (Alfano, et al., *J. Bacteriol.,* 177:4553–56 (1995), which is hereby incorporated by reference).

Figure 1B:
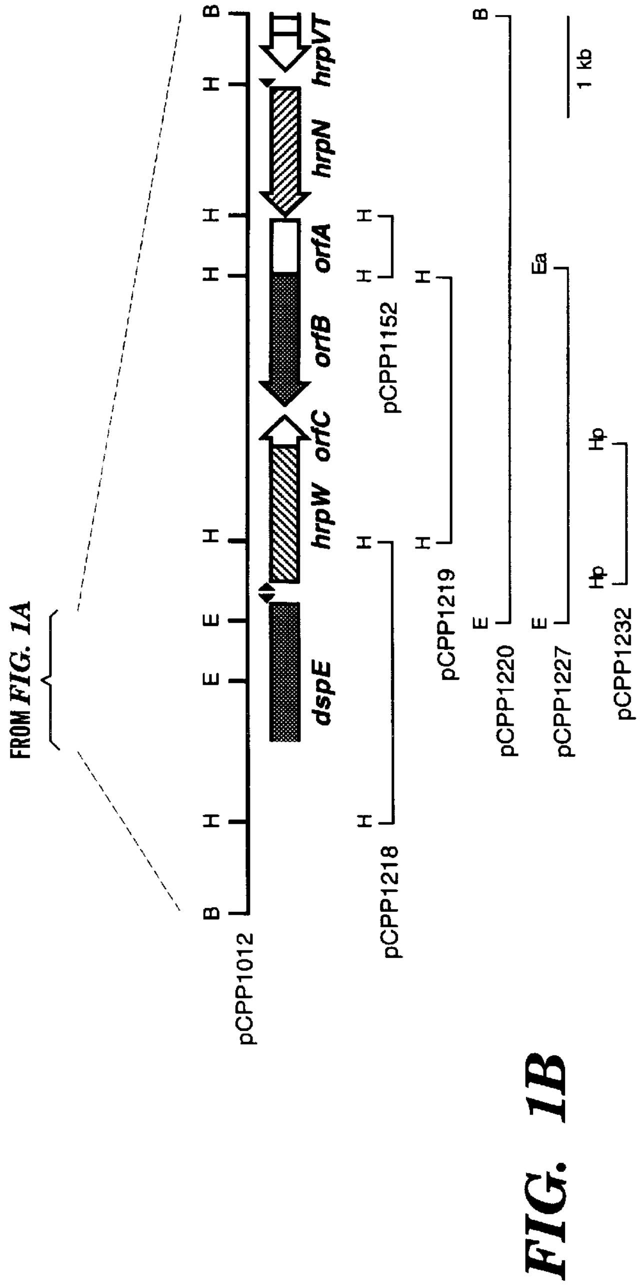
FIG. 1B shows the location of hrpW which encodes a Gly-rich protein, and subclones of pCPP1012 used in the study. Boxes and arrow boxes indicate genes or open reading frames; filled triangles are putative HrpL-dependent promoters. Restriction sites: B, BamHI; E, EcoRI; H, HindIII, Ea, EagI; Hp, HpaI.
Figure 2:
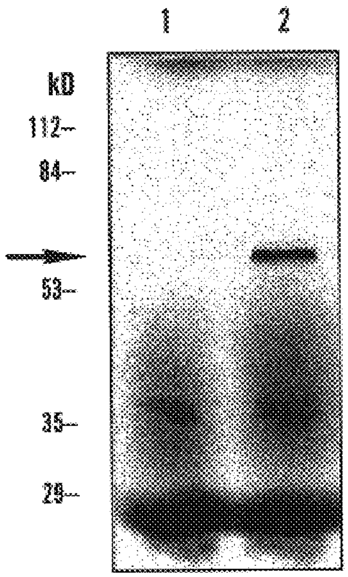
FIG. 2 shows the expression of hrpW by a T7 RNA polymerase-directed gene expression system. Lanes 1, *E. coli*DH5α(pGP1-2/pBC SK (−)); 2, *E. coli*DH5α(pGP1-2/pCPP1232). The arrow between 84 kD and 53 kD points to the band in lane 2 corresponding to the HrpW protein.

Example 10—Identification of a Gene Encoding a Glycine-Rich Protein.

hrpN mutants pCPP430-T5 and pCPP450-T5 in *E. coli* exhibited residual HR-eliciting activity (FIG. 5A, panels 2 and 4), suggesting the existence of another HR elicitor in the clones. The DNA downstream of hrpN, where pCPP430 and pCPP450 overlap, therefore, was subcloned and its sequence was determined. This revealed four open reading frames, designated ORF A, ORF B, ORF C and hrpW (FIG. 1B). A putative HrpL-dependent promoter (Bogdanove, et al., *J. Bacteriol.*, 178:172014 30 (1996) and Kim et al., *J. Bacteriol.*, 179:1690–97 (1997), which are hereby incorporated by reference), CGGAACC-$N_4$-C-$N_{10}$-CCACTCAAT (SEQ. ID. No. 3), was found 58-bp upstream of the hrpW start codon, suggesting that the expression of hrp W is controlled by HrpL, an alternate sigma factor (Wei, et al., *J. Bacteriol.,* 177:6201–10 (1995), which is hereby incorporated by reference). hrpW in pCPP1232 (FIG. 1B) was expressed using a T7 RNA polymerase/promoter system, and a specific protein band with an apparent molecular weight of ca. 60-kDa resulted (FIG. 2). This is larger than its expected size of 45-kDa. The same size band, however, was observed from the supernatant of *E. amylovora* (FIG. 4), indicating that the aberrant size of the protein is not a cloning artifact.

Figure 3:
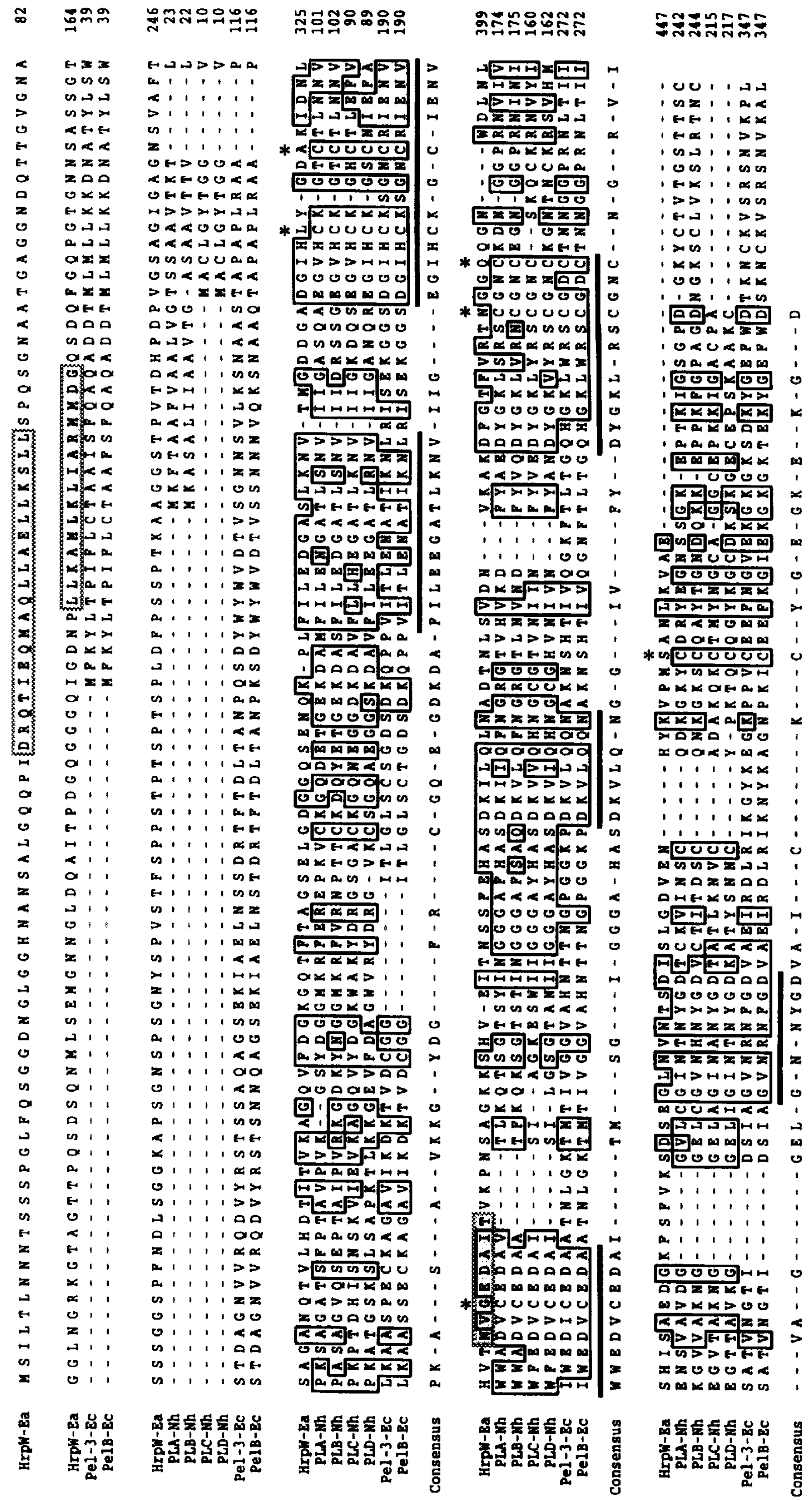
FIG. 3 shows the alignment of HrpW with pectate lyases of *Nectria haematococca*, mating type VI (*Fusarium solani* f. sp. pisi) and of *Erwinia carotovora* subsp. *carotovora*. The sequences were aligned by the PILEUP program (GCG software package, Version 7.3) with default parameters, and an alignment was manually edited using LINEUP program in the same package. Conserved residues are boxed, highly conserved regions are underlined, and potential α-helices in HrpW are shaded.

Example 11—Predicted Features of the hrpW Product.

hrpW was deducted to encode a protein of 447-aa residues, which is acidic (pl-4.5), hydrophilic, rich in Gly, Ser, and Asn, low in Glu, Arg, Trp, and Tyr, and lacking in Cys (FIG. 3). These properties are similar to harpins, although the primary structure of HrpW seemed not homologous to any of them. The sequence of HrpW suggests that the protein is composed of two domains: the N-terminal Gly-and Ser-rich domain and the C-terminal domain homologous to PLs (see below). About two-thirds of Gly and Ser are located in the N-terminal region. The Gly and Ser content of the first 240-aa residues is 17.5% and 14.2%, respectively. The N-terminal region could be divided into five subregions, and contained two sequences (residues 40–59 and 131–145) that may form amphipathic α-helices. The first 39 residues of the N-terminus contains many Gly, Ser, Leu, and Asn, but few charged or aromatic amino acids. Similarly, the region that connects the two potential α-helices has high Gly, Asn, and Gln content, but no aromatic residues. Residues 146–232 contain several repeats of Ser/Thr-Pro/Ser/Thr-Pro/Ser/Thr, suggesting that this region might be a linker (Gilkes, et al., *Microbiol. Rev.,* 55:303–15 (1991), which is hereby incorporated by reference).

Example 12—C-terminus of HrpW is Homologous to Pectate Lyases.

Database searches using BLAST and FASTA algorithms (Altschul, et al., *J. Mol. Biol.,* 215:403–10 (1990) and Pearson, et al., *Proc. Natl., Acad. Sci. USA,* 85:2444–48 (1988), which are hereby incorporated by reference) indicated that the C-terminal region of HrpW is homologous to PLA-D of *Nectria haematococcan* mating type VI (*Fusarium solani* f. sp. pisi) (Gonzalez, et al., *J. Bacteriol.,* 174:6343–49 (1992), Guo, et al., *J. Bacteriol.,* 177: 7070–77 (1995), Guo, et al., *Arch. Biochem. Biophys.,* 323:352–60 (1995), and Guo, et al., *Arch. Biochem. Biophys.,* 332:305–12 (1996), which are hereby incorporated by reference). BLAST P( ) values and FASTA E( ) values from runs with default parameters were 4.0e–14 to 3.03–10 and 2.7e–08 to 1e–06, respectively. Based on BESTFIT alignments, HrpW was 27–33% identical to the fungal PLs and the Z-scores were 8.14 to 13.3 Also, database search with PLs of *N. haematococca* showed that they are homologs of Pel-3 and PelB of *Erwinia carotovora* subsp. *carotovora* (Liu, et al., *Appl. Env. Microbiol.,* 60:2545–52 (1994) and Heikinheimo, et al., *Mol. Plant-Microbe Interact.,* 8:207–17 (1995), which are hereby incorporated by reference) (BLASTP P( ) values ranged from 9.0e–15 to 8.6e–10, and BESTFIT identities were 31–36%). These fungal PLs and *E. carotovora* Pel-3/PelB, together with HrpW, form a class distinct from other PL families. From an alignment of the proteins, five highly conserved blocks were recognizable (FIG. 3). The seven members share 20 identical residues of which five are Gly. The PHD algorithm predicted &-sheets and loops for the PL-homology region of HrpW, except for the sequence at residues 329–336 which has a propensity to form an α-helix (FIG. 3). Intriguingly, HrpW does not contain any Cys, which are conserved among PLs in the class. In addition, PL activity of HrpW was not detected using the several tests described in the materials and methods.

Example 13—Production and Secretion of HrpW are hrp-dependent.

Figure 4A:
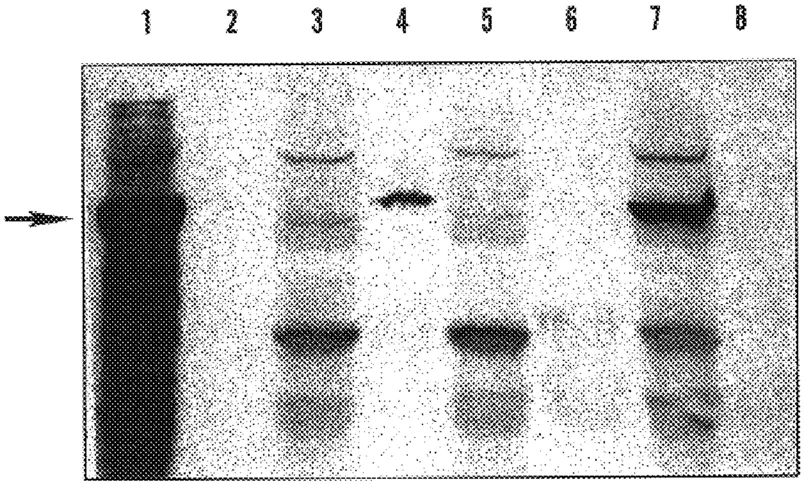
FIGS. 4A and B are immunoblots showing the hrp-dependent production and secretion of HrpW in *E. amylovora*. Lanes in FIG. 4: 1, *E. coli* DH5α(pGP1-2/pCPP1232); 2, HrpN; 3, whole cell preparation ("CP") of Ea321; 4, supernatant preparation ("SP") of Ea321; 5, CP of Ea321-K49; 6, SP of Ea321-K49; 7, CP of Ea321-G84; 8, SP of Ea321-G84. Lanes in FIG. 4B: 1, *E. coli* DH5α(pGP1-2/pCPP1232); 2, HrpN; 3, CP of Ea273; 4, SP of Ea273; 5, CP of Ea321-K49; 6, SP of Ea321-K49; 7, CP of Ea321-G73; 8, SP of Ea321-G73.
Figure 4B:
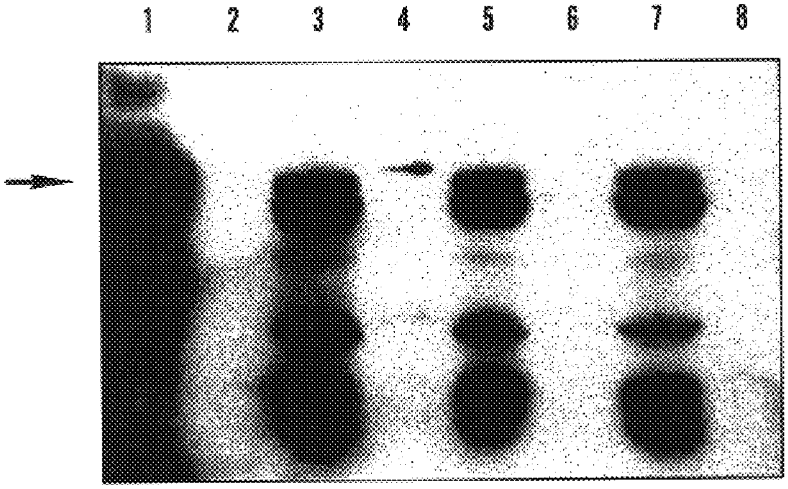

An immunoblot with anti-HrpW antibodies detected HrpW only from supernatant preparations of *E. amylovora* Ea321 and Ea273, indicating that HrpW is efficiently secreted (FIG. 4). HrpW was not found in preparations from hrpL mutants Ea321-K49 and Ea273-K49, demonstrating that expression of hrpW is hrpL-dependent. In addition, HrpW either was not detected or restricted to the whole cell preparations of hrp secretion mutants Ea321-G84 and Ea273-G73, respectively. Thus, secretion of HrpW is Hrp pathway-dependent. Anti-HrpW antibodies did not react with HrpW (FIG. 4, lane 2), suggesting structural differences between the two elicitors.

Example 14—HrpW Induces Rapid Tissue Necrosis on Plants in a Heat-stable and Protease-sensitive Manner.

Figure 5A:
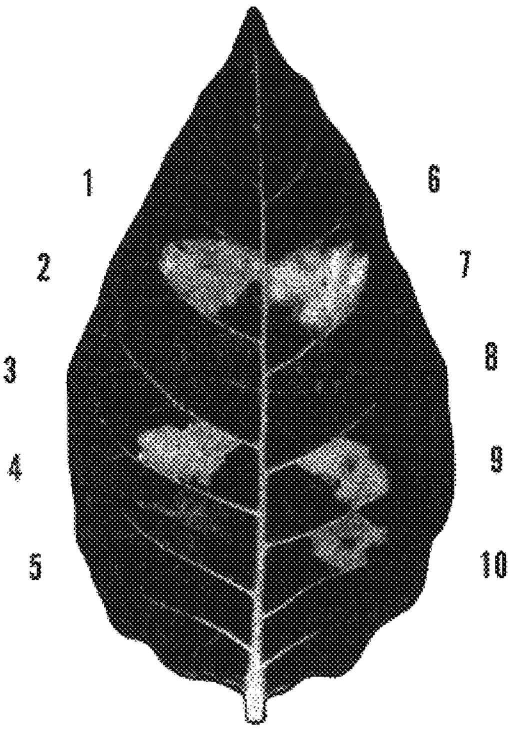
FIG. 5A shows a tobacco leaf showing residual hypersensitive response ("HR") eliciting activity of hrpN mutants, and the HR induced by HrpN and HrpW. Panels: 1, *E. coli*DH5(pCPP430); 2, *E. coli*DH5(pCPP430-T5); 3, *E. coli*MC4100(pCPP450); 4, *E. coli*MC4100(pCPP450-T5); 5, 5 mM $KPO_4$ buffer (pH 6.5); 6, *E. amylovora* Ea321; 7, *E. amylovora* Ea321-T5; 8, HrpN CFEP (contains 0.5 mg/ml of HrpN); 9, HrpW preparation (0.5 mg/ml) eluted from the gel containing proteins from *E. coli*DH5α(pGP1-2/pCPP1232); 10, preparation made from *E. coli*DH5α(pGP1-2/pBC SK (−)) in the same manner as 9. The picture was taken 3 days after infiltration.

From the predicted properties of HrpW, it is inferred to be an HR elicitor. To test this possibility, the partially purified protein was infiltrated into tobacco leaves. The infiltrated area began to collapse after 8–12 hr, and typical tissue necrosis, indistinguishable from that elicited by HrpN, developed 24–36 hr after inoculation (FIG. 5A, panel 9). HrpW induced tissue necrosis in tobacco at concentrations of 1.1 $\mu$M (50 $\mu$g/ml). HrpW also caused necrosis in African violet, geranium, tomato, pepper, *Kalanchoe diagremontiana*, and *Arabidopsis thaliana*, but not in soybean. A heat-treated preparation of HrpW still caused rapid necrosis in tobacco leaves, indicating the heat-stable nature of the activity (FIG. 5A, panel 2). On the other hand, treatment of HrpW with 3 mg/ml protease (type XIV; Sigma, St. Louis, Mo.) for 1 hr destroyed HR-eliciting activity.

Example 15—Elicitation by HrpW Requires Plant Metabolism.

Figure 5B:
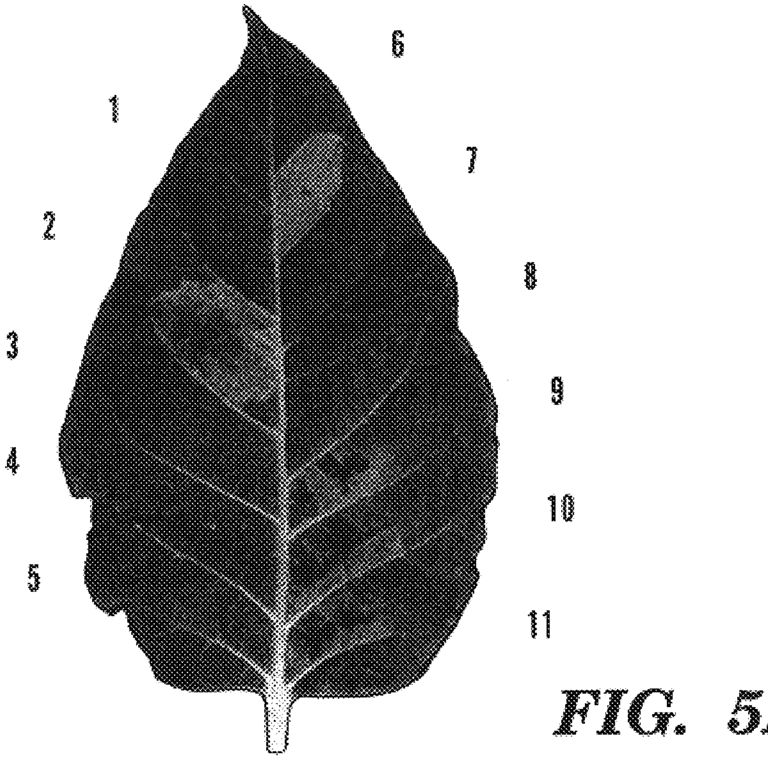
FIG. 5B shows suppression of the HrpW-induced HR by inhibitors of plant metabolism. Panels: 1, 5 mM $KPO_4$ buffer (pH 6.5); 2, HrpW CFEP; 3, HrpN CFEP+cycloheximide; 4, HrpW CFEP+$LaCl_3$; 5, HrpW CFEP+$Na_3VO_4$; 6, HrpN CFEP; 7, HrpN CFEP+cycloheximide; 8, HrpN CFEP+$Na_3VO_4$; 9, PelE in 10 mM Tris-HCl (pH 7.8); 10, PelE+cycloheximide; 11, PelE+$Na_3VO_4$. CFEPs contain 0.1 mg/ml of HrpW of HrpN. The picture of the tobacco leaf was taken 36 hours after infiltration.

A major question was whether the tissue necrosis caused by HrpW is due to a mechanism comparable to harpins (He, et al., *Cell,* 73:1255–66 (1993) and He, et al., *Mol. Plant-Microbe Interact.,* 7:289–92 (1994), which are hereby incorporated by reference). Coinfiltration of HrpW CFEP with the metabolic inhibitors cycloheximide, lanthanum chloride, or sodium vanadate (targets are 80S ribosome, $Ca^{2+}$ channels, ATPases/Y-phosphateses, respectively) prevented the HR (FIG. 5B, panels 3–5), like HrpN CFEP with the inhibitors (FIG. 5B, panels 7–8). This indicates that active plant metabolism is needed for the HrpW-induced HR. Tobacco leaves infiltrated with PelE of *E. chrysanthemi* EC 16 also exhibited rapid tissue necrosis (FIG. 5B, panel 9). However, necrosis caused by PelE occurred faster and the collapsed area was translucent, darker, softer, and easily crushed as compared to that elicited by harpins. In addition, PelE induced tissue necrosis irrespective of the presence of inhibitors (FIG. 5B, panels 10–11).

Example 16—N-terminal Region is Sufficient for HR Elicitation.

A fragment of hrpW encoding the N-terminal 226 residues, designated HrpW(1-226), was constructed, and the production of HrpW(1-226) was confirmed. Typical HR developed 24–36 hr after infiltration of HrpW(1-226) CFEP into tobacco leaves, though the activity was weaker than that of full-length HrpW. That HrpW(1-226) are produced stably and elicits the HR independently of the C-terminal region support the two-domain structure of HrpW derived from the sequence data.

Example 17—hrpW is Conserved Among Strains of *E. amylovora.*

Figure 6:
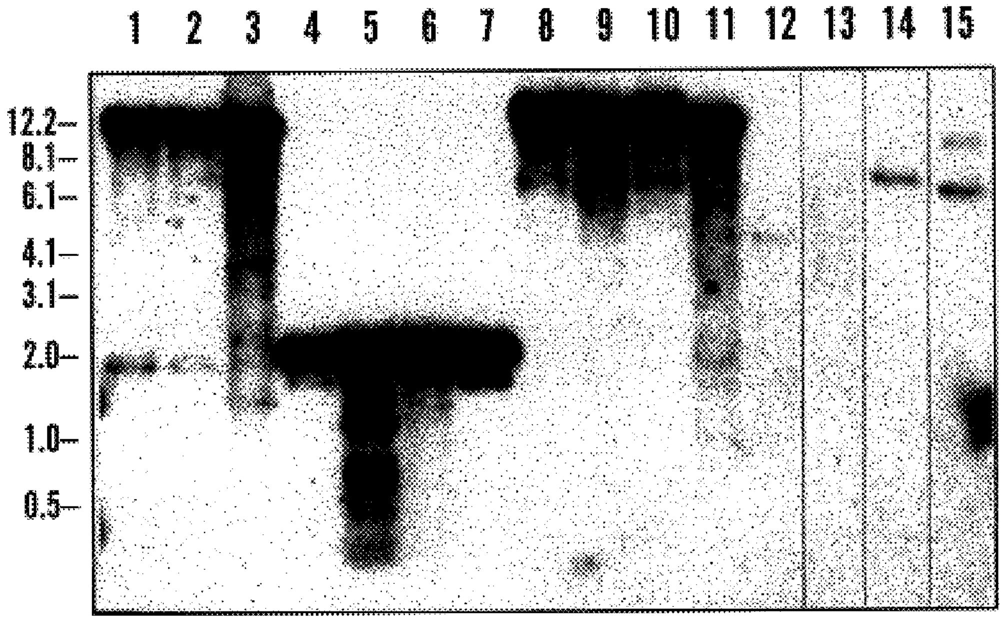
FIG. 6 shows a Southern blot which indicates that hrpW of *E. amylovora* Ea321 is present in other bacteria. Genomic DNA of strains was probed with a 1.4-kb HpaI fragment that contains Ea321 hrpw. Lanes: 1, Ea321; 2, Ea266; 3, Ea273; 4, Ea246; 5, Ea510; 6, Ea528; 7, Ea574; 8, Ea546; 9, Ea557; 10, Ea562; 11, Ea587; 12, *E. carotovora* subsp. *carotovora* ATCC15713; 13, *E. mallotivora* 1818; 14, *E. salicis* 1822; 15, pCPP2157 of *E. chrysanthemi* EC16.

The presence of hrpW in other bacteria was examined by Southern hybridization. Under high stringency conditions, single bands were observed for each of the ten strains of *E. amylovora* tested. The sizes of the restriction bands suggested three different groups. When low stringency conditions were used, hybridizing bands were visible from several other species of *Erwinia* such as *E. carotovora*, and *E. salicis*, and pCPP2157, a clone containing the hrp gene cluster of *E. chrysanthemi* (Bauer, et al., *Mol. Plant-Microbe Interact.,* 8:484–91 (1995), which is hereby incorporated by reference) (FIG. 6).

Previously, at most only one harpin was known from each bacterium. However, *E. amylovora* encodes HrpW, a harpin distinct from the first harpin described (HrpN; Wei et al., *Science,* 257:85–88 (1992), which is hereby incorporated by reference). Southern analysis suggests that hrpW exists in several other *Erwinia* species, suggesting a role for HrpW in pathogenesis. Furthermore, sequence comparison indicated that EXP-60 (renamed to HrpW of *P. syringae* pv. tomato (Yuan, et al., *J. Bacteriol.,* 178:6399–6402 (1996), which is hereby incorporated by reference) is homologous to HrpW of *E. amylorova.*

Analysis suggests that HrpW is a multidomain protein comprised of the N-terminal Gly/Ser-rich domain and the C-terminal PL-homology domain. That HrpW has homology to PLs was surprising, because *E. amylovora* is believed to be non-pecolytic (Seemüller, et al., *Phytopathology,* 66:433–36 (1976), which is hereby incorporated by reference). Besides, no pectic enzyme function has been suggested for harpins (Alfano, et al., *Plant Cell,* 8:1683–98 (1996), which is hereby incorporated by reference). Although PL activity was not detected, HrpW is not the first PL homolog for which pectic enzyme activity function has not been demonstrated. Some plant pollen proteins are PL homologs and pectic enzyme function has been suspected from the pollen-specific expression of the encoding genes (Wing, et al., *Plant Mol. Biol.,* 14:17–28 (1990), which is hereby incorporated by reference); however, they do not have detectable enzyme activity (Dircks, et al., *Plant Physiol. Biochem.,* 34:509–20 (1996), which is hereby incorporated by reference). HrpW may differ in substrate specificity from its homologs, or it may lack the pectic enzyme function like α-lactalbumins, which are homologs of lysozymes but do not have lysozyme function (McKenzie, et al., *Adv. Prot. Chem.,* 41:173–315 (1991), which is hereby incorporated by reference). Alternatively, instead of lyase function, HrpW may have only a pectic substance-binding function (Kurosky, et al., *Proc. Natl., Acad. Sci. USA,* 77:3388–92 (1980), which is hereby incorporated by reference).

HrpW is exceptional as a PL homolog in several respects. It does not posses the N-terminal signal peptide that is recognized by the Sec machinery; rather, it is secreted via a type III pathway. It does not contain any Cys residues conserved in PLs, which may have structural and functional roles. Furthermore, HR elicitation by HrpW depends on plant metabolism. Southern data suggests that *E. caratovora* has a hrpW homolog different from pel-3/pelB. Considering its dependence on the hrp system and the lack of detectable PL activity, the role of HrpW in pathogenesis may not be for simple degradation of cell wall for utilization as a carbon source; rather, through possible pectic enzyme activity or cell wall-binding activity, it may assist the Hrp pilus (Roine, et al., *Proc. Natl. Acad. Sci. USA,* 94:3459–64 (1997), which is hereby incorporated by reference) or other pathogenicity/virulence/avirulence proteins in getting through the cell wall.

Several evolutionary related groups of pectic enzymes are apparent based on amino acid comparisons and structural analyses: i) a class called the "extracellular PL superfamily" (Henrissat, et al., *Plant Physiol.,* 107:963–76 (1995), and references therein, which are hereby incorporated by reference) that includes two PL families of plant pathogenic bacteria, *Bacillus subtilis* and some fungi, PelX of *E. caratovora*, pectin lyases, and plant pollen and style proteins, ii) a class comprising periplasmic PLs of *Yersinia pseudotuberculosis* and *E. caratovora* (Hinton, et al., *Mol. Microbiol.,* 3:1785–96 (1989), which is hereby incorporated by reference) and KdgC of *E. chrysanthemi* (Condemine, et al., *Mol. Microbiol.,* 5:2191–2202 (1991), which is hereby incorporated by reference), iii) a class that consists of PLs of *N. haematococca*, and Pel-3/PelB of *E. carotovora*, iv) PelX and PelL of *E. chrysanthemi* (Alfano, et al., *J. Bacteriol.,*

177:4553–56 (1995) and Lojkowska, et al., *Mol. Microbiol.*, 16:1183–95 (1995), which are hereby incorporated by reference), and v) recently reported PelZ of *E. chrysanthemi* and *E. carotovora* (Pissavin, et al., *J. Bacteriol.*, 178:7187–96 (1996), which is hereby incorporated by reference). The third class of homology group has not yet been recognized as a protein family, although members have been mentioned in the literature (Henrissat, et al., *Plant Physiol.*, 107:963–76 (1995) and Liao, et al., *Mol. Plant-Microbe Interact.*, 9:14–21 (1996), which are hereby incorporated by reference). Therefore, this third class, to which HrpW of *E. amylovora* belongs, will be referred to as "class III pectate lyases" to differentiate it from the two earlier classes, which should be called "class I" and "class II". Members of the "class III PLs" appear to be widespread among plant pathogens. Besides HrpW in *P. syringae* pv. tomato, *E. chrysanthemi* has PelI which is very closely related to Pel-3/PelB of *E. carotovora*.

It is enigmatic how harpins apparently heterogeneous in sequence and possibly in structure can induce the same plant response. The "cell-killing" action of harpins appears not due to potential enzymatic or toxic function such as making pores in the cell membrane; HR activity is heat-stable (Wei, et al., *Science*, 257:85–88 (1992), He, et al., *Cell*, 73:1255–66 (1993), and Arlat, et al., *EMBO J.*, 13:543–53 (1994), which are hereby incorporated by reference), requires plant metabolism (He, et al., *Cell*, 73:1255–66 (1993), and He, et al., *Mol. Plant-Microbe Interact.*, 7:289–92 (1994), which are hereby incorporated by reference), and fragments can elicit the reaction (Arlat, et al., *EMBO J.*, 13:543–53 (1994), Alfano, et al., *Mol. Microbial.*, 19:715–28 (1996), and Laby, et al., *Molecular Studies on Interactions Between Erwinia amylovora and Its Host and Non-Host Plants*, Cornell University, Ithaca, N.Y. (1997), which are hereby incorporated by reference). Avr proteins induce the HR on plants carrying corresponding resistance genes (Staskawicz, et al., *Science*, 268:661–67 (1995), which is hereby incorporated by reference). It seems less probable that harpins evoke the HR by the same kind of mechanism, although downstream signaling events could be shared. Possible signaling mechanisms that lead to the HR against harpins were discussed by Novacky and colleagues (Hoyos, et al., *Mol. Plant-Microbe Interact.*, 9:608–16 (1996), which is hereby incorporated by reference).

It appears that Gly/Ser richness may be important for HR-eliciting function of harpins, because non-overlapping fragments that elicit the HR include Gly/Ser-rich regions (Arlat, et al., *EMBO J.*, 13:543–53 (1994), Alfano, et al., *Mol. Microbial.*, 19:715–28 (1996), and Laby, et al., *Molecular Studies on Interactions Between Erwinia amylovora and Its Host and Non-Host Plants*, Cornell University, Ithaca, N.Y. (1997), which are hereby incorporated by reference). In support of the hypothesis, a truncated HrpW containing the N-terninal Gly/Ser-rich domain has HR-eliciting ability. On the other hand, HR elicitation by fragments is weaker as compared to whole protein (Laby, et al., *Molecular Studies on Interactions Between Erwinia amylovora and Its Host and Non-Host Plants*, Cornell University, Ithaca, N.Y. (1997) and this work, which are hereby incorporated by reference) indicating that other part (s) of harpins contribute to the full-strength HR. It will be of interest to determine whether plant cell wall Gly-rich proteins ("GRPs"), the encoding genes of which are expressed during xylogenesis and after wounding or viral infection (Showalter, A.M., *Plant Cell*, 5:9–23 (1993), which is hereby incorporated by reference), possess the ability to cause cell death.

Harpins appear to be targeted to outer parts of plant cells such as the cell wall. They can elicit the HR when exogenously applied to plant tissue by infiltration. When harpins are added to cell-suspension culture, $K^+$ efflux and alkalinization of the medium, referred to as exchange reaction ("XR"), followed by cell death occurs (Wei, et al., *Science*, 257:85–88 (1992) and Popham, et al., *Physiol. Mol. Plant Pathol.*, 47:39–50 (1995), which is hereby incorporated by reference). However, the XR does not occur in protoplast culture. In addition, HrpZ antibodies localize HrpZ outside of plant cells and not in protoplasts, and the alkalinization and the localization is blocked by a chelating agent that extracts $Ca^{2+}$ and pectin (Hoyos, et al., *Mol. Plant-Microbe Interact.*, 9:608–16 (1996), which is hereby incorporated by reference). The homology of HrpW to PLs is consistent with a model in which the site of harpin action is the plant cell wall.

Type III systems of animal pathogens secrete many proteins involved in pathogenesis (for example, see Cornelis, et al., *Mol. Microbiol.*, 23:861–67 (1997), which is hereby incorporated by reference). Until recently, however, only harpins have been shown to be delivered by the type III machinery of plant pathogens. Recent evidence suggests that multiple proteins are secreted through the Hrp pathway, and that several Avr proteins are transferred directly into the plant cell by way of the Hrp secretion machinery (Gopalan, et al., *Plant Cell*, 8:1095–1105 (1996), Leister, et al., *Proc. Natl. Acad. Sci. USA*, 93:15497–15502(1996), Scofield, et al., *Science*, 274:2063–65 (1996), Tang, et al., *Science*, 274:2060–63 (1996), and Van Den Ackerveken, et al., *Cell*, 87:1307–16 (1996), which are hereby incorporated by reference).

It is interesting that hrpW is flanked by dspE and ORF B (FIG. 1B), which are homologs of avrE of *P. syringae* and avrRxv of *X. campestris* pv. vesicatoria, respectively. The linkage of harpin genes and homologs of non-host avr genes provides a hint of relationships between them in pathogenesis. Harpins might in reality be a class of Avr proteins, or Avr proteins may be actually virulence proteins. PopA of *P. solanacearum* GMI1000 elicits the HR only in resistant petunia lines (Arlat, et al., *EMBO J.*, 13:543–53 (1994), which is hereby incorporated by reference). Also, expression of the Avr phenotype is controlled by the hrp system, and some avr genes possess virulence or pathogenicity functions (Dangl, *Curr. Top. Microbiol. Immunol.*, 192:99–118 (1994), which is hereby incorporated by reference). Indeed, dspE is a pathogenicity factor. Thus, the region of the *E. amylovora* genome where harpin genes and avr homologs reside may constitute an arsenal for proteins used to bombard different parts of the host cell. Elucidating their specific targets and effects in the HR and pathogenesis will be pivotal to understand mechanisms of plant-bacterial interactions.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated hypesensitive response eliciting protein or polypeptide selected from the group consisting of (i) a protein or polypeptide comprising an amino acid sequence-of SEQ. ID. No. 2, (ii) a protein or polypeptide encoded by a DNA molecule comprising a nucleotide sequence of SEQ. ID. No. 1, and (iii) a protein or polypeptide encoded by a nucleic acid molecule which hybridizes to a DNA molecule comprising a nucleotide sequence of SEQ. ID. No. 1 under stringent conditions comprising hybridization at a temperature of about 65° C. in a hybridization medium comprising about 1 M NaCl.

2. An isolated protein or polypeptide according to claim 1 wherein the protein or polypeptide comprises an amino acid sequence of SEQ. ID. No. 2.

3. An isolated protein or polypeptide according to claim 1, wherein the protein or polypeptide is encoded by a nucleic acid molecule which hybridizes to a DNA molecule comprising a nucleotide sequence of SEQ. ID. No. 1 under stringent conditions comprising hybridization at a temmperature of about 65° C. in a hybridization medium comprising about 1 M NaCl.

4. An isolated protein or polypeptide according to claim 1, wherein the protein or polypeptide is encoded by a DNA molecule comprising a nucleotide sequence of SEQ. ID. No. 1.

5. A composition comprising a protein or polypeptide according to claim 1 and a carrier.

6. A composition according to claim 5 further comprising an additive selected from the group consisting of fertilizer, insecticide, fungicide, nematacide, and mixtures thereof.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 1344 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

```
ATGTCAATTC TTACGCTTAA CAACAATACC TCGTCCTCGC CGGGTCTGTT CCAGTCCGGG     60

GGGGACAACG GGCTTGGTGG TCATAATGCA AATTCTGCGT TGGGGCAACA ACCCATCGAT    120

CGGCAAACCA TTGAGCAAAT GGCTCAATTA TTGGCGGAAC TGTTAAAGTC ACTGCTATCG    180

CCACAATCAG GTAATGCGGC AACCGGAGCC GGTGGCAATG ACCAGACTAC AGGAGTTGGT    240

AACGCTGGCG GCCTGAACGG ACGAAAAGGC ACAGCAGGAA CCACTCCGCA GTCTGACAGT    300

CAGAACATGC TGAGTGAGAT GGGCAACAAC GGGCTGGATC AGGCCATCAC GCCCGATGGC    360

CAGGGCGGCG GGCAGATCGG CGATAATCCT TTACTGAAAG CCATGCTGAA GCTTATTGCA    420

CGCATGATGG ACGGCCAAAG CGATCAGTTT GGCCAACCTG GTACGGGCAA CAACAGTGCC    480

TCTTCCGGTA CTTCTTCATC TGGCGGTTCC CCTTTTAACG ATCTATCAGG GGGGAAGGCC    540

CCTTCCGGCA ACTCCCCTTC CGGCAACTAC TCTCCCGTCA GTACCTTCTC ACCCCCATCC    600

ACGCCAACGT CCCCTACCTC ACCGCTTGAT TTCCCTTCTT CTCCCACCAA AGCAGCCGGG    660

GGCAGCACGC CGGTAACCGA TCATCCTGAC CCTGTTGGTA GCGCGGGCAT CGGGGCCGGA    720

AATTCGGTGG CCTTCACCAG CGCCGGCGCT AATCAGACGG TGCTGCATGA CACCATTACC    780

GTGAAAGCGG GTCAGGTGTT TGATGGCAAA GGACAAACCT TCACCGCCGG TTCAGAATTA    840

GGCGATGGCG GCCAGTCTGA AAACCAGAAA CCGCTGTTTA TACTGGAAGA CGGTGCCAGC    900

CTGAAAAACG TCACCATGGG CGACGACGGG GCGGATGGTA TTCATCTTTA CGGTGATGCC    960

AAAATAGACA ATCTGCACGT CACCAACGTG GGTGAGGACG CGATTACCGT TAAGCCAAAC   1020

AGCGCGGGCA AAAAATCCCA CGTTGAAATC ACTAACAGTT CCTTCGAGCA CGCCTCTGAC   1080

AAGATCCTGC AGCTGAATGC CGATACTAAC CTGAGCGTTG ACAACGTGAA GGCCAAAGAC   1140

TTTGGTACTT TTGTACGCAC TAACGGCGGT CAACAGGGTA ACTGGGATCT GAATCTGAGC   1200

CATATCAGCG CAGAAGACGG TAAGTTCTCG TTCGTTAAAA GCGATAGCGA GGGGCTAAAC   1260

GTCAATACCA GTGATATCTC ACTGGGTGAT GTTGAAAACC ACTACAAAGT GCCGATGTCC   1320

GCCAACCTGA AGGTGGCTGA ATGA                                          1344
```

(2) INFORMATION FOR SEQ ID NO:2:

(i) SEQUENCE CHARACTERISTICS:
(A) LENGTH: 447 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:2:

-continued

```
Met Ser Ile Leu Thr Leu Asn Asn Asn Thr Ser Ser Ser Pro Gly Leu
1               5                   10                  15

Phe Gln Ser Gly Gly Asp Asn Gly Leu Gly Gly His Asn Ala Asn Ser
            20                  25                  30

Ala Leu Gly Gln Gln Pro Ile Asp Arg Gln Thr Ile Glu Gln Met Ala
        35                  40                  45

Gln Leu Leu Ala Glu Leu Leu Lys Ser Leu Leu Ser Pro Gln Ser Gly
    50                  55                  60

Asn Ala Ala Thr Gly Ala Gly Gly Asn Asp Gln Thr Thr Gly Val Gly
65                  70                  75                  80

Asn Ala Gly Gly Leu Asn Gly Arg Lys Gly Thr Ala Gly Thr Thr Pro
                85                  90                  95

Gln Ser Asp Ser Gln Asn Met Leu Ser Glu Met Gly Asn Asn Gly Leu
            100                 105                 110

Asp Gln Ala Ile Thr Pro Asp Gly Gln Gly Gly Gly Gln Ile Gly Asp
        115                 120                 125

Asn Pro Leu Leu Lys Ala Met Leu Lys Leu Ile Ala Arg Met Met Asp
    130                 135                 140

Gly Gln Ser Asp Gln Phe Gly Gln Pro Gly Thr Gly Asn Asn Ser Ala
145                 150                 155                 160

Ser Ser Gly Thr Ser Ser Ser Gly Gly Ser Pro Phe Asn Asp Leu Ser
                165                 170                 175

Gly Gly Lys Ala Pro Ser Gly Asn Ser Pro Ser Gly Asn Tyr Ser Pro
            180                 185                 190

Val Ser Thr Phe Ser Pro Pro Ser Thr Pro Thr Ser Pro Thr Ser Pro
        195                 200                 205

Leu Asp Phe Pro Ser Ser Pro Thr Lys Ala Ala Gly Gly Ser Thr Pro
    210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
                245                 250                 255

Asp Thr Ile Thr Val Lys Ala Gly Gln Val Phe Asp Gly Lys Gly Gln
            260                 265                 270

Thr Phe Thr Ala Gly Ser Glu Leu Gly Asp Gly Gly Gln Ser Glu Asn
        275                 280                 285

Gln Lys Pro Leu Phe Ile Leu Glu Asp Gly Ala Ser Leu Lys Asn Val
    290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
                325                 330                 335

Val Lys Pro Asn Ser Ala Gly Lys Lys Ser His Val Glu Ile Thr Asn
            340                 345                 350

Ser Ser Phe Glu His Ala Ser Asp Lys Ile Leu Gln Leu Asn Ala Asp
        355                 360                 365

Thr Asn Leu Ser Val Asp Asn Val Lys Ala Lys Asp Phe Gly Thr Phe
    370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
```

-continued

```
            420                 425                 430

Asn His Tyr Lys Val Pro Met Ser Ala Asn Leu Lys Val Ala Glu
        435                 440                 445


(2) INFORMATION FOR SEQ ID NO:3:

     (i) SEQUENCE CHARACTERISTICS:
          (A) LENGTH: 31 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:3:

CGGAACCNNN NCNNNNNNNN NNCCACTCAA T                                   31
```